United States Patent [19]

Sekine et al.

[11] Patent Number: 5,324,728
[45] Date of Patent: Jun. 28, 1994

[54] NAPHTHOIC ACID DERIVATIVE

[75] Inventors: Yasuo Sekine, Yokohama; Tetsuaki Yamaura, Niiza; Masato Nishimura, Hachioji; Eri Kojima, Tokyo; Yasuko Emoto, Sagamihara; Yasushi Higashide, Hachioji, all of Japan

[73] Assignee: Fujirebio Inc., Tokyo, Japan

[21] Appl. No.: 801,501

[22] Filed: Dec. 2, 1991

[30] Foreign Application Priority Data

Nov. 30, 1990 [JP] Japan .................................. 2-330004

[51] Int. Cl.$^5$ .................. C07D 401/00; C07D 241/04; C07D 295/00; A61K 31/495
[52] U.S. Cl. ..................................... 514/252; 514/218; 514/255; 514/317; 514/318; 514/319; 514/326; 514/327; 514/397; 514/398; 514/399; 514/400; 514/424; 514/426; 514/438; 514/471; 540/575; 544/360; 544/379; 544/383; 544/393; 544/396; 544/397; 544/400
[58] Field of Search .............. 544/360, 379, 396, 383, 544/393, 397, 400, 379; 846/400; 540/575; 549/65; 514/218, 252, 255, 318, 319, 326, 327, 438, 471, 397, 398, 399, 400; 548/517, 544

[56] References Cited
U.S. PATENT DOCUMENTS 4,673,684  6/1987  Wakabayashi et al. ............ 544/273

Primary Examiner—Cecilia Tsang
Attorney, Agent, or Firm—Sherman and Shalloway

[57] ABSTRACT

A naphthoic acid derivative represented by the following general formula or a salt thereof:

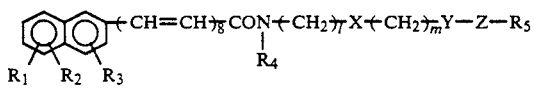

wherein
$R_1$, $R_2$ and $R_3$ are each independently a hydrogen atom, a halogen atom, a hydroxyl group, a lower alkyl group, a lower alkoxy group, a lower alkanoyloxy group, a hydroxy-lower alkyl group, a lower alkoxy-lower alkyl group, a lower alkanoyloxy-lower alkyl group or an aralkyloxy group;
$R_4$ is a hydrogen atom or a lower alkyl group;
$R_5$ is a substituted or unsubstituted aryl group or a substituted or unsubstituted heteroaromatic group;
X is a group

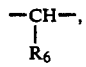

a cycloalkylene group, a bivalent nitrogen-containing heterocyclic group, or a group

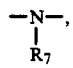

—$R_8$—NH— or —NH—$R_8$, where $R_6$ and $R_7$ are each a hydrogen atom or a lower alkyl group and $R_8$ is a cycloalkylene group, or $R_6$ and $R_7$, together with $R_4$, may form an alkylene group of 1–3 carbon atoms;

Y is —S(O)$_p$—, —(CH$_2$)$_n$— or —O—;

Z is a substituted or unsubstituted alkylene group or a single bond;
l is an integer of 0–4;
m is an integer of 0–8;
n is 0 or 1;
p is an integer of 0–2; and
g is 0 or 1.

The compound is useful as an antiallergic agent.

4 Claims, No Drawings

NAPHTHOIC ACID DERIVATIVE

The present invention relates to a novel naphthoic acid derivative. More particularly, the present invention relates to a naphthoic acid derivative represented by the following general formula or a salt thereof:

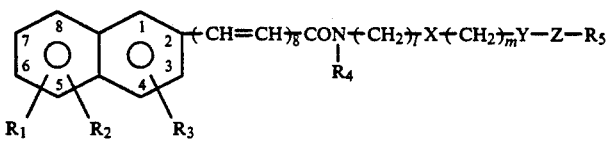

wherein
- $R_1$, $R_2$ and $R_3$ are each independently a hydrogen atom, a halogen atom, a hydroxyl group, a lower alkyl group, a lower alkoxy group, a lower alkanoyloxy group, a hydroxy-lower alkyl group, a lower alkoxy-lower alkyl group, a lower alkanoyloxy-lower alkyl group or an aralkyloxy group;
- $R_4$ is a hydrogen atom or a lower alkyl group;
- $R_5$ is a substituted or unsubstituted aryl group or a substituted or unsubstituted heteroaromatic group;
- X is a group

a cycloalkylene group, a bivalent nitrogen-containing heterocyclic group, or a group

—$R_8$ NH— or —NH—$R_8$—, where $R_6$ and $R_7$ are each a hydrogen atom or a lower alkyl group and $R_8$ is a cycloalkylene group, or $R_6$ and $R_7$, together with $R_4$, may form an alkylene group of 1–3 carbon atoms;
- Y is —$S(O)_p$—, —$(CH_2)_n$— or —O— or a single bond;
- Z is a substituted or unsubstituted alkylene group or a single bond;
- l is an integer of 0–4;
- m is an integer of 0–8;
- n is 0 or 1;
- p is an integer of 0–2; and
- g is 0 or 1;

a process for producing said naphthoic acid derivative; and applications of said naphthoic acid derivative or a salt thereof to pharmaceutical fields, particularly as an antiallergic agent.

The naphthoic acid derivative represented by general formula (I) has a 5-lipoxygenase-inhibiting action and is useful as a drug, particularly as an antiallergic agent.

Diseases caused by allergic reaction include bronchial asthma, nasitis, seasonal conjunctivitis, hives, etc. It is known that these diseases are connected with chemical mediators such as histamine, leukotrienes, prostaglandins, thromboxanes (TX's), platelet-activating factor (PAF) and the like, and various antiallergic agents have been developed which act on individual chemical mediators. These allergic agents, however, are not fully satisfactory for treatment of allergosis which is caused by the complicated interaction between chemical mediators. Hence, researches were made in order to find out compounds which can inhibit a plurality of chemical mediators simultaneously and, as a results, amide compounds were proposed (U.S. Pat. No. 4,673,684).

These amide compounds have a leukotriene production-suppressing action by the 5-lipoxygenase-inhibiting action and a histamine antagonism, but show no sufficient effect for treatment of allergosis caused by complicated allergic reaction. Therefore, the development of a more effective allergic agent capable of affecting a plurality of chemical mediators simultaneously, is strongly desired.

The present inventors made study in order to solve the above-mentioned problem and found novel naphthoic acid derivative having a naphthalene ring represented by the above general formula (I), which has a plurality of actions, i.e. a 5-lipoxygenase-inhibiting action, a $TXA_2$ synthesis enzyme-inhibiting action ($TXA_2$ antagonism), a histamine antagonism and a cell membrane-stabilizing action for histamine-liberating mast cells. The present invention has been completed based on the above finding.

In the present specification and appended claims, the term "lower" is used to indicate that the group or compound to which the term is prefixed has 6 or less, preferably 4 or less carbon atoms.

"Halogen atom" includes a fluorine atom, a chlorine atom, a bromine atom and an iodine atom.

"Alkyl group" can be a straight chain or a branched chain. Therefore, "lower alkyl group" includes, for example, methyl, ethyl, propyl, isopropyl, butyl, sec-butyl, isobutyl, tert-butyl, pentyl and hexyl.

"Lower alkoxy group" is a lower alkyloxy group in which the lower alkyl portion has the above meaning. It includes, for example, methoxy, ethoxy, propoxy, isopropoxy, butoxy, tert-butoxy, pentoxy and hexyloxy.

"Lower alkanoyloxy group" is a (lower alkyl)-CO—O— group in which the lower alkyl portion has the above meaning. It includes, for example, acetoxy, propionyloxy and butyryloxy.

"Hydroxy-lower alkyl group" is a hydroxyl-substituted lower alkyl group and includes, for example, hydroxymethyl, 2-hydroxyethyl, 2- or 3-hydroxypropyl, and 4-hydroxybutyl.

"Lower alkoxy-lower alkyl group" is a lower alkoxy-substituted lower alkyl group in which the lower alkoxy portion and the lower alkyl portion each have the above meaning. It includes, for example, methoxymethyl, methoxyethyl, ethoxymethyl, ethoxyethyl, methoxypropyl, propoxymethyl and methoxybutyl.

"Lower alkanoyloxy-lower alkyl group" is a lower alkanoyloxy-substituted lower alkyl group in which the lower alkanoyloxy portion and the lower alkyl portion each have the above meaning. It includes, for example, acetoxymethyl, acetoxyethyl, propoxymethyl and propoxyethyl.

"Aralkyloxy group" refers to an aryl-substituted lower alkoxy group, in which the aryl includes not only carbon ring groups such as phenyl, naphthyl and the like but also hereto ring groups such as pyridyl, imidazolyl, pyrazinyl, furyl, thienyl, pyrrolyl, oxazolyl and the like. Specific examples of the aralkyloxy group includes, for example, benzyloxy, phenetyloxy, phenylpropyloxy, phenylbutyloxy, phenylpentyloxy, phenylhexyloxy, 2-pyridylmethyloxy, 3-pyridylmethyloxy, 4-pyridylmethyloxy, 1-imidazolylmethyloxy, 2-pyradinylmethyloxy, 2-furylmethyloxy, 3-furylmethyloxy, 2-thienylmethyloxy, 3-thienylmethyloxy, 1-pyrrolylmethyloxy and 2-oxazolylmethyloxy.

"Aryl group" in the term "substituted or unsubstituted aryl group" can be monocyclic or polycyclic and includes phenyl, naphthyl, etc. "Heteroaromatic group" in the term "substituted or unsubstituted heteroaromatic group" is an aromatic unsaturation-containing heterocyclic group containing at least one, preferably 1-4 heteroatoms selected from nitrogen, oxygen and sulfur atoms, preferably a 5 to 6 membered heterocyclic group, and includes, for example, furyl, thienyl, pyrrolyl, oxazolyl, thiazolyl, imidazolyl, pyridyl and pyrazinyl.

Possible as the substituent on the above aryl group or heteroaromatic group, are a halogen atom, a lower alkyl group, a lower alkoxy group, a lower alkylthio group, a lower alkoxy-lower alkyl group, a lower alkanoyl group, a lower alkoxycarbonyl group, a trifuluoromethyl group, a carboxyl group, a lower alkoxycarbonyl group, a hydroxyl group, a nitro group, a cyano group, an amino group, a phenyl group, an imidazolyl group, an imidazolylmethyl group, an alkylenedioxy group, etc. The aryl or heteroaromatic group may have 1–5, particularly 1–2 substituents selected from the above groups.

Specific examples of "substituted aryl group" and "substituted heteroaromatic group" are 2-chlorothienyl, 3-chlorothienyl, 2-methoxythienyl, 2-hydroxythienyl, 2-aminothienyl, 3-aminothienyl, 2-acetoxythienyl, 2-(1-imidazolyl)thienyl, 2-methylthienyl, 3-ethylthienyl, 4-acetoxy-3-methoxythienyl, 3-chlorofuryl, 3-bromofuryl, 2-iodofuryl, 3-methoxyfuryl, 3-hydroxyfuryl, 2-acetoxyfuryl, 2-(1-imidazolyl)methylfuryl, 3-trifluorofuryl, 3-methylfuryl, 2-ethylfuryl, 3,4-dimethylfuryl, 3-ethyl-4-methoxyfuryl, pyridyl, 3-fluoropyridyl, 3,4-dichloropyridyl, 3,4-dimethoxypyridyl, 3,4-dihydroxypyridyl, 3-amino-4-hydroxypyridyl, 2-(1-imidazolyl)methylpyridyl, pyridyl, 2-(1-imidazolyl)-pyridyl, 4-(1-imidazolyl)methylpyridyl, 3,4-ditrifluoromethylpyridyl and 4-methylpyridyl.

"Cycloalkylene group" is a cyclic alkylene group having preferably 3–8, particularly 5–7 carbon atoms, and includes, for example,

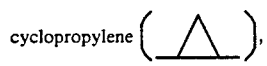

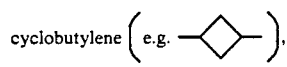

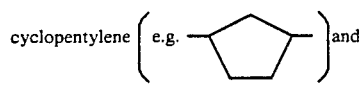

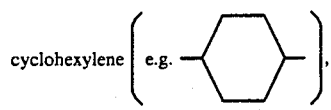

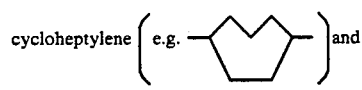

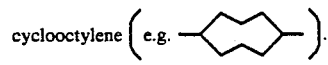

"Bivalent nitrogen-containing heterocyclic group" is a saturated heterocyclic group containing at least 1, preferably 1 to 2 nitrogen atoms in the cycle, and is preferably 4 to 8 membered, particularly 4 to 6 membered. Examples of the bivalent nitrogen-containing heterocyclic group are

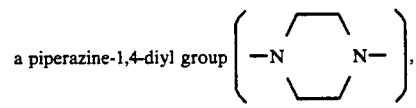

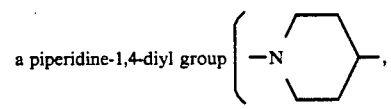

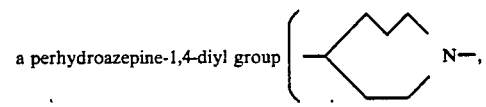

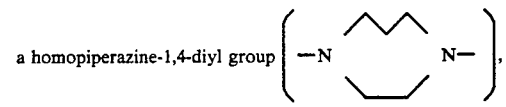

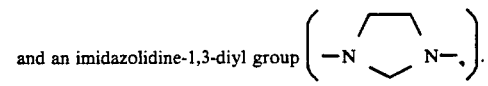

"Alkylene group" can be a straight chain or a branched chain and includes, for example, methylene, ethylene, 1,3-propylene, 1,2-propylene, 1,4-butylene, 1,2-butylene, pentamethylene, hexamethylene, heptamethylene and octamethylene.

In the above general formula (I), $R_1$, $R_2$ and $R_3$ may be attached to any position of the naphthalene ring. However, it is generally preferable that $R_1$ and/or $R_2$ be at the 5- and/or 7-position and $R_3$ be at the 2-position. Preferably, one of $R_1$ and $R_2$ is a hydrogen atom and the other is a hydroxyl group, a lower alkoxy group (particularly, a methoxy group), a lower alkanoyloxy group (particularly, an acetyloxy group) or a pyridyl-substituted lower alkoxy group (particularly, a pyridylmethyloxy or pyridylethyloxy group). Also preferably, $R_3$ is a hydroxyl group, a lower alkoxy group (particularly, a methoxy group) or a lower alkanoyloxy group (particularly, an acetyloxy group).

Examples of the $$-\underset{\underset{R_4}{|}}{N}-(CH_2)-X-$$

portion of general formula (I) when X is a group $$-\underset{\underset{R_6}{|}}{CH}- \quad \text{or} \quad -\underset{\underset{R_7}{|}}{N}-$$

and $R_6$ or $R_7$, together with $R_4$, forms an alkylene group of 1-3, preferably 1-2 carbon atoms, are a piperazine-1,4-diyl group $\left(-N\underset{\diagdown\diagup}{\diagup\diagdown}N-\right)$, a piperidine-1,4-diyl group $\left(-N\underset{\diagdown\diagup}{\diagup\diagdown}-\right)$, a perhydroazepine-1,4-diyl group $\left(-N\underset{\diagdown\diagup}{\diagup\diagdown\diagup}-\right)$, a homopiperazine-1,4-diyl group $\left(-N\underset{\diagdown\diagup}{\diagup\diagdown\diagup}N-\right)$, and an imidazolidine-1,3-diyl group $\left(-N\underset{\diagdown\diagup}{\diagup\diagdown}N-\right)$.

Of them, $-N\underset{\diagdown\diagup}{\diagup\diagdown}N-$ are $-N\underset{\diagdown\diagup}{\diagup\diagdown}-$ preferable.

In the "substituted or unsubstituted alkylene group" represented by Z in general formula (I), the alkylene group preferably has generally 1-4, preferably 1-2 carbon atoms. The alkylene group may be mono-substituted by a substituted or unsubstituted aryl group or a substituted or unsubstituted heteroaromatic group, each of which is the same as or different from $R_5$.

Preferable examples of the substituted or unsubstituted aryl group or the substituted or unsubstituted heteroaromatic group, each represented by $R_5$, are a phenyl group, a naphthyl group, a mono- or dihalophenyl group, a lower alkylphenyl group, a lower alkoxyphenyl group, a lower alkylthiophenyl group, a nitrophenyl group, a cyanophenyl group, a lower alkoxycarbonylphenyl group, a lower alkanoylphenyl group, a biphenylyl group, a mono- or ditrifluoromethylphenyl group, a methylenedioxyphenyl group, a thienyl group, a halothienyl group, a furyl group and a pyridyl group.

However, Z is particularly preferably —CH₂—, $$-\underset{\underset{|}{CH}-}{\overset{R_9}{|}}$$

or a single bond, where $R_9$ is a phenyl group, a halophenyl group or a pyridyl group.

In general formula (I), X is preferably $-CH_2-, \quad -\underset{\underset{CH_3}{|}}{N}-, \quad -N\underset{\diagdown\diagup}{\diagup\diagdown}N-,$ $-N\underset{\diagdown\diagup}{\diagup\diagdown}-, \quad -N\underset{\diagdown\diagup}{\diagup\diagdown\diagup}N-,$ etc. $R_4$ is preferably a hydrogen atom, and q is desirably 0.

Y is $-S(O)_p-$, $-(CH_2)_n-$ or $-O-$. The $-S(O)_p-$ is a sulfide group when p is 0, a sulfinyl group when p is 1, and a sulfonyl group when p is 2; the $-(CH_2)_n-$ is a single bond when n is 0, and a methylene group when n is 1. Y is preferably a sulfinyl group (—S—), —CH₂—, —O— or a single bond, and particularly preferably —S—, —O— or a single bond.

m is preferably 0-4.

Typical examples of the compound of general formula (I) provided by the present invention are as follows except for those shown in Exampels which are described later.

N-[2-[4-(Benzhydryloxy)piperidino]ethyl]-6,7-dihydroxy-2-naphthamide, N-[2-[4-(Benzhydryloxy)-piperidino]ethyl]-3-(6,7-dihydroxynaphthoyl)-(E)-propeneamide, N-[2-[4-(Benzhydryloxy)-piperidono]ethyl-3-(5,8-dihydroxyanaphthoyl)-(E)-2-propeneamide, N-[2-[4-(Benzhydryloxy)piperidino]ethyl]-5,8-dihydroxy-2-naphthamide, N-[2-[4-(Benzhydryloxy)piperidino]-3-(3,7-dihydroxynaphthoyl)-(E)-2-propeneamide, N-[2-[4-(Benzhydryloxy)piperidino]-3-(3,5-dihydroxynaphthoyl)-(E)-2-propeneamide, N-[2-[4-(Benzhydryloxy)piperidino]ethyl]-6-hydroxy-7-pyridylmethoxy-2-naphthamide, N-[2-[4-(Benzhydryloxy)piperidino]ethyl]-6-hydroxy-7-[2-(pyridyl)ethoxy]-2-naphthamide, N-[2-[4-(Benzhydryloxy)-piperidino]ethyl]-6-hydroxy-7-[3-(pyridyl)propyloxy]-2-naphthamide, N-[2-[4-(Benzhydryloxy)piperidino]ethyl]-6-hydroxy-7-[2-(1-imidazolyl)ethoxy]-2-naphthamide, N-[2-[4-(Benzhydryloxy)piperidino]ethyl]-3-(6-hydroxy-7-pridylmethoxynaphthoyl)-(E)-2-propeneamide, N-[2-[4-(Benzhydryloxy)piperidino]ethyl]-3-[6-hydroxy-7-[2-(limidazolyl)ethoxy]naphthoyl]-(E)-2-propeneamide, N-[2-[4-(Benzhydryloxy)piperidino]ethyl]-8-hydroxy-5-pyridylmethoxy-2-naphthamide, N-[2-[4-(Benzhydryloxy)-piperidino]ethyl]-8-hydroxy-5-[2-(pyridyl)ethoxy]-2-naphthamide, N-[2-[4-(Benzhydryloxy)piperidino]ethyl]-8-hydroxy-5-[3-(pyridyl)propyloxy]-2-naphthamide, N-[2-[4-(Benzhydryloxy)-piperidino]ethyl]-8-hydroxy-5-[2-(1-imidazolyl)ethoxy-2-naphthamide, N-[2-[4-Benzhydryloxy)piperidino]ethyl]3-(8-hydroxy-5-pyridylmethoxynaphthoyl)-(E)-2-propeneamide, N-[2-[4-(Benzhydryloxy)piperidino]ethyl]-3-[8-hydroxy-5-[2-(1-imidazolyl)ethoxy]naphthoyl]-(E)-2-propeneamide, N-[2-[4-(Benzhydryloxy)-piperidino]ethyl]-3-(3-hydroxy-7-pyridylmethoxynaphthoyl)-(E)-2-propeneamide, N-[2-[4-(Benzhydryloxy)- piperidino]ethyl]-3-[3-hydroxy-7-[2-(pyridyl)ethoxynaphthoyl]-(E)-2-propeneamide, N-[2-[4-(Benzhydryloxy)piperidino]ethyl]-3-[3-hydroxy-7-[3-(pyridyl)-propyloxynaphthoyl]-(E)-2-propeneamide, N-[2-[4-(Benzhydryloxy)piperidino]ethyl]-3-[3-hydroxy-7-[2-(1-imidazolyl)ethoxy]naphthoyl]-(E)-2-propeneamide, N-[2-[4-(Benzhydryloxy)piperidino]ethyl]-3-hydroxy-5-[2-(pyridyl)ethoxy]-2-naphthamide, N-[2-[4-(Benzhydryloxy)piperidino]ethyl]-3-hydroxy-5-[3-(pyridyl)-propyloxy]-2-naphthamide, N-[2-[4-(Benzhydryloxy)-piperidino]ethyl]-3-hydroxy-5-[2-(1-imidazolyl)ethoxy]-2-naphthamide, N-[2-[4-(Benzhydryloxy)-piperidino]ethyl]-3-(3-hydroxy-5-pyridylmethoxynaphthoyl)-(E)-2-propeneamide, N-[2-[4-(Benzhydryloxy)-piperidino]ethyl]-3-[3-hydroxy-5-[2-(1-imidazolyl)ethoxy]naphthoyl]-(E)-2-propeneamide, N-[2-[methyl-[2-(4-chlorophenyl)-phenylmethoxy]ethyl]aminoethyl]-3-hydroxy-5-pyridylmethoxy-2-naphthamide, N-[2-[methyl[2-[(4-chlorophenyl)-(2-pyridyl)methoxy]ethyl]aminoethyl]-3-hydroxy-5-pyridylmethoxy-2-naphthamide, N-[2-[methyl-[2-[(2-pyridyl)-phenylmethoxy]ethyl]aminoethyl]-3-hydroxy-5-pyridylmethoxy-2-naphthamide, N-[2-[methyl-[3-[(4-chlorophenyl)-(2-pyridyl)methoxy]propyl]aminoethyl]-3-hydroxy-5-pyridylmethoxy-2-naphthamide, N-[3-[4-(benzhydryloxy)-piperidino]propyl]-3-hydroxy-5-pyridylmethoxy-2-naphthamide, N-[2-[4-[(2-pyridyl)-phenylmethoxy]-piperidino]ethyl]-3-hydroxy-5-pyridylmethoxy-2-naphthamide, N-[2-[4-[(4-chlorophenyl)-(2-pyridyl)methoxy]piperidino]ethyl]-3-hydroxy-5-pyridylmethoxy-2-naphthamide, N-[2-[4-(benzhydryloxy)piperidino]ethyl]-3-hydroxy-5-pyridylmethoxy-2-naphthamide, N-[2-[4-[(2-pyridyl)-phenylmethoxy]homopiperidino]ethyl]-3-hydroxy-5-pyridylmethoxy-2-naphthamide, N-[2-[4-(benzhydryloxy)cyclohexylamino]ethyl]-3-hydroxy-5-pyridylmethoxy-2-naphthamide, N-[2-[4-(benzhydrylamino)cyclohexylamino]ethyl]-3-hydroxy-5-pyridylmethoxy-2-naphthamide, N-[2-[4-(benzhydrylamino)piperidino]ethyl]-3-hydroxy-5-pyridylmethoxy-2-naphthamide, In the compound of the present invention, preferable are those represented by the following formula:

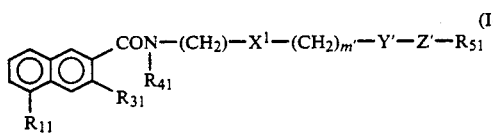
(I-1)

wherein
$R_{11}$ is a hydroxyl group, a lower alkanoyloxy group or a pyridyl-substituted lower alkoxy group;
$R_{31}$ is a hydroxyl group or a lower alkanoyloxy group;
$R_{41}$ is a hydrogen atom;
$R_{51}$ is a phenyl group, a halophenyl group or a thienyl group;
$X^1$ is

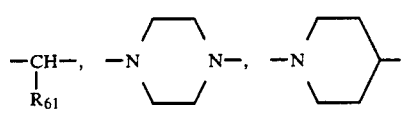

or where
$R_{61}$ is a hydrogen atom or, together with $R_{41}$, may form an alkylene group

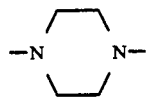

of 1-2 carbon atoms;
$Y^1$ is —S—, —O— or a single bond;
$Z^1$ is —CH$_2$— or

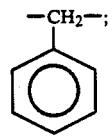

$l$ is an integer of 0–4; and
$m'$ is an integer of 0–4.

Particularly preferable are those compounds of formula (I-1) wherein $R_{11}$ is a pyridylmethoxy;
$R_{31}$ is a hydroxyl group;
$R_{41}$ is a hydrogen atom;
$R_{51}$ is a phenyl group;
$X^1$ is

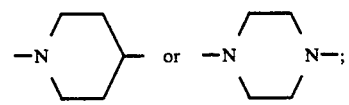

$Y^1$ is —O— or a single bond;
$Z^1$ is

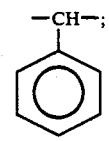

$l$ is 2–4; and
$m'$ is 0.

The compound of general formula (I) can be present in the form of acid addition salt when the formula (I) compound has an amino group. Examples of such a salt are inorganic acid salts such as hydrochloride, hydrobromide, phosphate, sulfate and the like, and organic acid salts such as acetate, propionate, lactate, citrate and the like. Pharmaceutically acceptable acid addition salts are particularly preferable.

The compound of general formula (I) according to the present invention can be produced, for example, by reacting a carboxylic acid represented by the following general formula:

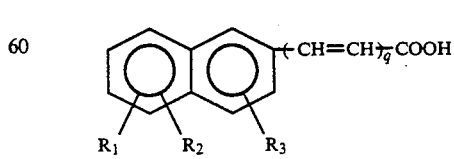
(II)

wherein $R_1$, $R_2$, $R_3$ and $q$ are as defined above, or a reactive derivative thereof with an amine compound represented by the following general formula:

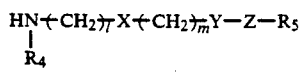   (III)

wherein $R_4$, $R_5$, X, Y, Z, l and m are as defined above.

The reaction between the carboxylic acid of formula (II) and the amine compound of formula (III) is an amidation reaction and can be conducted generally in the presence of a condensing agent according to an ordinary method. As the condensing agent, there can be used, for example, a carbodiimide reagent such as N,N'-dicyclohexylcarbodiimide (DCC), 1-ethyl-3-(3-dimethylaminopropyl)carbodiimide hydrochloride (WSC) and the like.

The amount of the amine compound of formula (III) used to the carboxylic acid of formula (II) is not strictly restricted, but is preferably 1–2 moles, particularly 1–1.3 moles per mole of the carboxylic acid of formula (II).

The reaction is desirably conducted generally in an inert solvent. Such a solvent includes, for example, halogenated hydrocarbons such as dichloromethane, chloroform, carbon tetrachloride and the like; ethers such as diethyl ether, tetrahydrofuran (THF), dimethoxyethane (DME), dioxane and the like; and amides such as dimethylformamide (DMF) and the like. They can be used singly or in admixture.

The reaction can be conducted generally at 0° C. to about 150° C., but preferably at 10°–100° C. in view of the efficiency.

In the above reaction, it is possible to use N,N-dimethylaminopyridine or the like as a catalyst.

The above amidation reaction may be conducted without using any condensing agent, that is, by converting the carboxylic acid of formula (II) to a reactive derivative thereof, for example, an active ester derivative, an acid halide, a mixed acid anhydride or the like and then reacting the reactive derivative with the amine compound of formula (III) in an inert solvent.

The active ester derivative of the formula (II) carboxylic acid can be produced according to an ordinary method. For example, it can be produced by condensing the formula (II) carboxylic acid with an alcohol such as N-hydroxysuccinimide, N-hydroxyphthalimide, 2-nitrophenol, 4-nitrophenol, 2,4-dinitrophenol or the like in the presence of a carbodiimide reagent in an inert solvent.

The halide of the formula (II) carboxylic acid includes, for example, carboxylic acid chloride and carboxylic acid bromide. The acid chloride can be produced according to an ordinary method, for example, by reacting the formula (II) carboxylic acid with a halogenating agent such as thionyl chloride, thionyl bromide, phosphorus pentachloride or the like in an inert solvent.

The mixed acid anhydride derivative of the formula (II) carboxylic acid can be produced according to an ordinary method, for example, by condensing the formula (II) carboxylic acid with an acid chloride such as ethyl chlorocarbonate, phenyl chlorocarbonate, pyvaloyl chloride, acetyl chloride, benzyl chloride or the like in the presence of a base in an inert solvent.

The reaction of the reactive derivative of the formula (II) carboxylic acid with the formula (III) amine compound can be conducted generally at about −20° C. to about 50° C., preferably 0°–20° C. using 1–2 moles, particularly 1–1.3 moles the formula (III) amine compound per mole of the reactive derivative of the formula (II) carboxylic acid.

The compound of formula (I) produced by the above amidation reaction can be separated and purified according to a per se known method, for example, colum chromatography, recrystallization, distillation or the like.

The compound of formula (I) wherein $R_1$, $R_2$ and/or $R_3$ is a lower alkanoyloxy group, can be converted by hydrolysis to a compound of formula (I) wherein the corresponding $R_1$, $R_2$ and/or $R_3$ is a hydroxyl group. This hydrolysis reaction can be conducted according to an ordinary method, for example, by using a base such as potassium carbonate, sodium carbonate, potassium hydrogen-carbonate, sodium hydrogencarbonate or the like in an inert solvent.

The naphthoic acid derivative of formula (I) having an amino group may be converted to a corresponding acid addition salt by reaction with a pharmaceutically acceptable acid according to an ordinary method.

The carboxylic acid of formula (II) used as a starting material in the above reaction, is known per se. It can be produced according to the method described in Reference Example 1, 2 or 3 which appears later, or a method similar thereto. Specific examples of the formula (II) carboxylic acid are 3-hydroxy-2-naphthoic acid, 3,5-dihydroxy-2-naphtoic acid, 3,7-dihydroxy-2-naphtoic acid, 3-acetoxy-2-naphtoic acid, 3,5-diacetoxy-2-naphtoic acid, 3,7-diacetoxy-2-naphtoic acid, 5-acetoxy-3-hydroxynaphtoic acid, 3-hydroxy-5-methoxynaphtoic acid, 3-hydroxy-5-(2-pyridylmethyl)naphtoic acid and 3,5-dimethoxy-2-naphtoic acid.

Meanwhile, the formula (III) amine compound can be produced by, for example, the method of the following reaction scheme A or B.

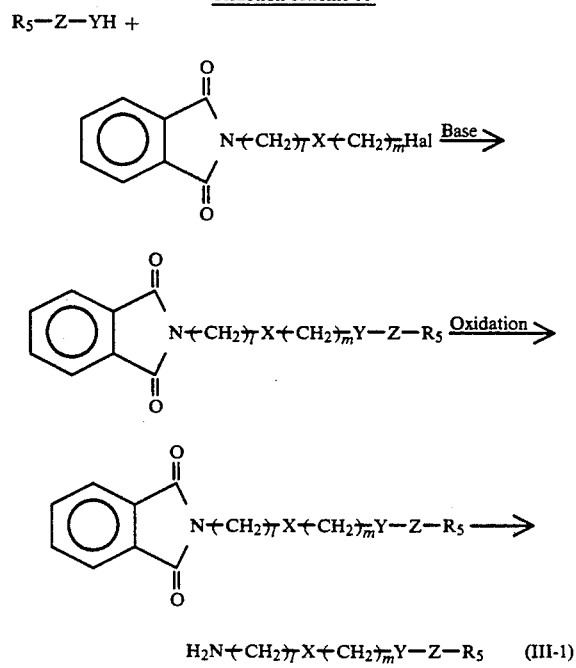

Reaction scheme B

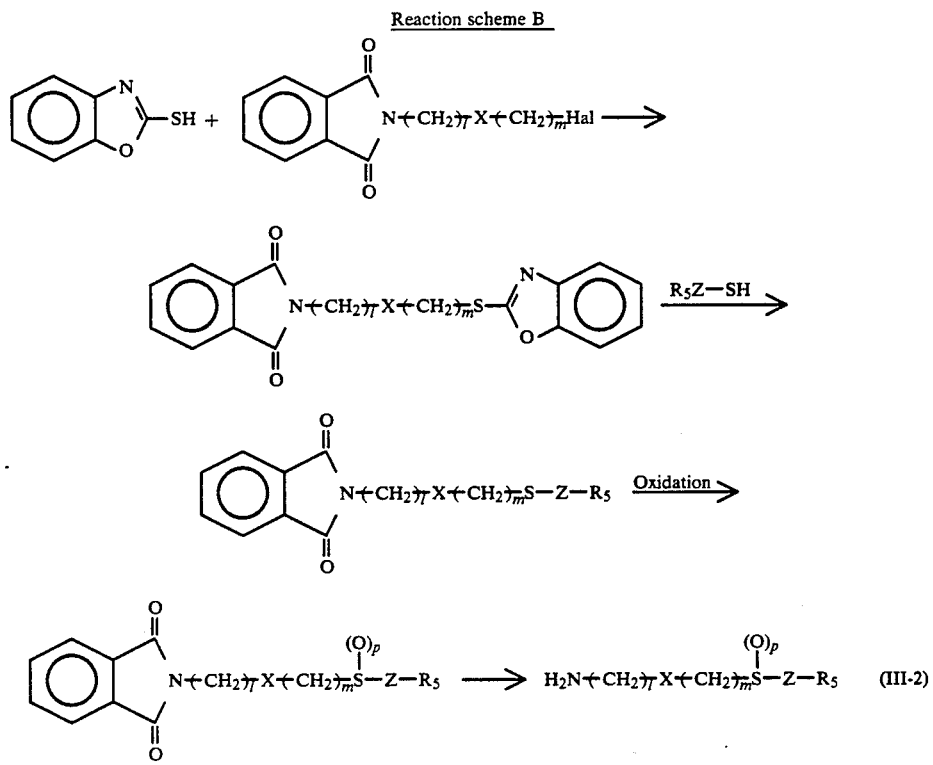

In the above formulas, $R_5$, X, Y, Z, l, m and p are as defined above, and Hal is a halogen atom.

As to the details of the reaction schemes A and B, the descriptions made in Reference Examples 4–8 which appear later, can be referred to.

The amine compound of formula (III) wherein X is a methylene group, can be produced from a thiol compound according to the method disclosed in Japanese Patent Application Laid-Open No. 297373/1988.

Typical examples of the formula (III) amine compound are 2-(3-furfurylmethylthio)ethaneamine, 2-(3-furfurylmethylsulfinyl)ethaneamine, 2-(3-furfurylmethylsulfonyl)ethaneamine, 2-(2-furfurylmethylthio)ethaneamine, 2-(2-furfurylmethylsulfinyl)ethaneamine, 2-(2-furfurylmethylsulfonyl)ethaneamine, 2-(2-thienylmethylthio)ethaneamine, 2-(benzhydryl)ethaneamine, (2-4-chlorophenylmethylthio)ethaneamine, 2-(2-pyridylmethylthio)ethaneamine, 2-(benzhydrylsulfonyl)ethaneamine, 2-(2-pyridyl-phenylmethylthio)ethaneamine, 2-{4-(1-imidazolylmethyl)phenylmethylthio}ethaneamine, 5-(2-thienylmethylthio)pentaneamine, 2-{(4-methoxyphenyl-2-thienyl)methylthio}ethaneamine, 2-{4-(1-imidazolyl)phenylmethylthio}ethaneamine, 3-(2-thienylmethylthio)propaneamine, 3-{3-(2-thienyl)propylthio}propaneamine, 3-{2-(2-thienyl)ethylthio}propaneamine, 2-{2-(2-thienyl)ethylthio}ethaneamine, 4-{3-(2-thienyl)propylthio}butaneamine, 4-(2-thienylmethylthio)butaneamine, 8-(2-thienylmethylthio)acetaneamine, 4-{2-(2-thienyl)thylthio} butaneamine, 2-(2-pyridylthio)ethaneamine, 2-(2-pyrimidylthio)ethaneamine, 2-(1-imidazol-2-ylthio)ethaneamine, 1-(2-aminoethyl)-4-{2-(2-thienyl)ethylthio} piperidine, 1-(2-aminoethyl)-4-diphenyl-methylthiopiperidine, N-(2-aminoethyl)-N'-{2-(2-thienylmethylthio)ethyl}piperazine, 2-[N-methyl-N'-{2-(2-thienylmethylthio)ethyl}amino]ethaneamine, N-(2-aminoethyl)-N'-{2-(diphenylmethylthio)ethyl)piperazine, 4-(2-aminoethyl)-1-≡2-(diphenylmethylthio)ethyl}piperidine, 1-(2-aminoethyl)-4-{2-(diphenylmethylthio)ethyl} homopiperazine, N-(2-aminoethyl)-N'-{2-{4-(1-imidazolylmethyl)phenylmethylthio}ethyl}piperazine, 4-(2-aminoethyl)-1-{2-{4-(1-imidazolylmethyl)phenylmethylthio)ethyl}piperidine, 1-(2-aminoethyl)-4-{2-{4-(1-imidazolylmethyl)phenylmethylthio}ethyl} homopiperazine, N-{2-(diphenylmethylthio)ethyl}piperazine, 4-{2-(diphenylmethylthio)ethyl}piperidine, N-{2-(diphenylmethylthio)ethyl}homopiperidine, N-{2-(4-(1-imidazolylmethyl}phenylmethylthio}ethyl} piperazine, 4-{2-{4-(1-imidazolylmethyl) phenylmethylthio}ethyl}piperidine, N-{2-{4-(1-imidazolylmethyl)phenylmethylthio}ethyl}homopiperidine, N-(2-aminoethyl)-N'-{2-{6-(1-imidazolylmethyl)pyridin-2-yl-methylthio}ethyl}piperazine, 4-(2-aminoethyl)-1-{2-{6-(1-imidazolylmethyl}pyridin-2-yl-methylthio}ethyl} piperidine, 1-(2-aminoethyl)-4-{2-{6-(1-imidazolylmethyl)pyridin-2-yl-methylthio}ethyl}ethyl}homopiperazine, N-(2-aminoetyl)-N'-{2-(2-pyridylphenylmethylthio)ethyl}piperazine, 4-(2-aminoethyl)-1-{2-(2-pyridylphenylmethylthio)ethyl}piperidine, 1-(2-aminoethyl)-4-{2-(2-pyridylphenylmethylthio)ethyl}homopiperidine, N-{2-(2-pyridylphenylmethylthio)ethyl}piperazine, 4-{2-(2-pyridyl-phenylmethylthio)ethyl}piperidine, N-{2-(2-pyridyl-phneylmethylthio)ethyl}homopiperidine, N-(2-aminoethyl)-N'-{2-{4-1-imidazolyl)phenylmethylthio}ethyl}piperazine, 4-(2-aminoethyl)-1-{2-{4-(1-imidazolyl)phenylmethylthio}ethyl}piperidine, 1-(2-aminoethyl)-4-{2-(4-(1-imidazolyl)phenylmethylthio}ethyl}homopiperazine, N-(2-aminoethyl)-N'-{2-(3-pyridylphenylmethylthio)ethyl}piperazine, 4-(2-aminoethyl)-1-{2-(3-pyridylphenylmethlthio)ethyl}piperidine, 1-(2-aminoethyl)-4-{2-(3-pyridylphenylmethylthio)ethyl}homopiperazine, N-(2-aminoethyl)-N'-{2-{4-(4-chlorophenyl)phenylmethylthio}piperazine, 4-(2- aminoethyl)-1-{2-{4-(4-chlorophenyl)phenylmethylthio}ethyl}piperidine, 1-(2-aminoethyl)-4-{2-{4-(4-chlorophenyl)phenylmethylthio}ethyl}homopiperazine, N-(2-aminoethyl)-N'-2-{di-(4-chlorophenyl)methylthio}ethyl}piperazine, 4-(2-aminoethyl)-1-{2-{di(4-chlorophenyl)methylthio}ethyl}piperidine, 4-(2-aminoethyl)-1-{2-{di-(4-chlorophenyl)methylthio}ethyl}homopiperazine, 2-(4-benzhydryl-1-piperazinyl)ethaneamine, 2-{4-(2-pyridyl-phenylmethyl)piperazino}ethaneamine, 2-{4-(3-pyridyl-phenylmethyl)piperazino}ethaneamine, 2-{4-(4-pyridylphenylmethyl)piperazino}ethaneamine and 2-{4-(benzhydryloxy)piperidino}ethaneamine.

The naphthoic acid derivative of formula (I) provided by the present invention has a 5-lipoxygenase-inhibiting action, a $TXA_2$ synthetase-inhibiting action (a $TXA_2$ antagonism), a histamine antagonism and a mast cell-stabilizing action, and is expected to find application as an antiallergic agent.

The above pharmacological actions of the present compound can be proven by the following tests.

TEST EXAMPLE 1

5-Lipoxygenase activity-inhibiting action

Rat basophil leukemia-1 cells were suspended in a 50 mM phosphate buffer solution (PBS) of pH 7.0 containing 1 mM of EDTA, 0.1% of gelatin and 14 μM of indometacin so that the resulting suspension contained $5 \times 10^7$ cels cells/ml ml. The suspension was subjected to an ultrasonic treatment and then to centrifugation (10,000G, 20 minutes). The resulting supernatant liquid was used as an enzymatic solution. 10 μl of a test compound solution was added to 460 μl of the enzymatic solution and a reaction was conducted at 37° C. for 5 minutes. Thereto were added 7.4 KBq of $^{14}C$-arachidonic acid and a 100 mM aqueous calcium chloride solution, and a reaction was conducted at 37° C. for 10 minutes. The reaction mixture was ice-cooled and then adjusted to pH 3 with 1N hydrochloric acid to terminate the reaction. Thereafter, extraction with 5 ml of chloroform was conducted. The extract was subjected to evaporation to dryness in the presence of nitrogen gas, and the residue was dissolved in a 2:1 mixture of chloroform and methanol. The solution was developed by thin-layer chromatography using Kieselgel 60 $F_{254}$, according to the method of Jakschik, B. A. et al. [Biachen. Biophys. Res. Commun. 95, 103 (1980)]. The radioactivity of 5-hydroxyeicosatetraenoic acid (5-HETE) was measured by a liquid scintillation counter (LSC-900 manufactured by Aroka) to determine the ratio of 5-HETE biosynthesis inhibition of test compound-added group to control group, after which there was determined a concentration of test compound at which the activity of 5-lipoxygenase was inhibited by 50%, i.e. an $IC_{50}$. The test compound was used in a diluted form by dissolving it in dimethyl sulfoxide. The results are shown in Tables 1, 2 and 3 which appear later.

TEST EXAMPLE 2

Membrane-stabilizing action

This test was conducted according to the method of Schwartz, J. et al. [Int. Arch. Allergy 30, 67 (1966)].

That is, 10 ml each of Hnak's balanced salt solution containing 10 units/ml of heparin was administered to rats intraperitoneally. After gentle massage of the abdomen for 2 minutes, peritoneal exudate cells (PEC) were obtained and washed 3 times with PBS containing 0.1% of bovine serum albumin (BSA). Mast cells in the suspension of PEC were stained with 0.2% of Neutral Red, and PEC were adjusted to a concentration of $4 \times 10^5$ mast cells/ml using PBS containing 0.1% of BSA. The cell suspension (50 μl) was incubated with 50 μl of a test compound solution at 37° C. for 5 minutes, then challenged with anti-egg albumin rat serum (50 μl, 1:40) and egg albumin (50 μl, 10 mg/ml) and further incubation was performed for 10 minutes. The reaction mixture was ice-cooled to terminate the reaction. Thereafter the number of mast cells undergoing degranulation was assessed under microscope observation to determine the menbrane-stabilizing action of the test compound. The results are shown in Table 1.

TABLE 1

| | 5-Lipoxygenase-inhibiting action $IC_{50}$ (M) | Membrane-stabilizing action $10^{-4}$ M (%) |
|---|---|---|
| Example 4 | $3.2 \times 10^{-7}$ | 53.7 |
| 5 | $4.1 \times 10^{-7}$ | 96.5 |
| 21 | $2.5 \times 10^{-7}$ | 100 |
| 34 | $1.5 \times 10^{-7}$ | 41 |
| 42 | $5.1 \times 10^{-6}$ | 60.1 |
| 43 | $1.1 \times 10^{-6}$ | 80.7 |

TEST EXAMPLE 3

Histamine antagonism

Guinea pigs were sacrificed and the tracheae were isolated. Each trachea was cut open at the center of the tracheal cartilage, and was cut in the vertical direction to separate into individual segments. Three of these segments were combined to form a tracheal chain. The tracheal chain was suspended in a Magnus tube filled with a Tyrode's solution (NaCl: 137 mX, KCl: 2.7 mM, $CaCl_2$: 1.8 nM, $MgCl_2$: 1.1 mM, $NaHPO_4$: 0.4 mM, $NaHCO_3$: 12.0 mM, glucose: 5.6 mM) kept at 37° C., while applying a load of 0.5 g. A mixed gas consisting of 95% of $O_2$ and 5% of $CO_2$ was constantly passed through the tube, and the contraction of the smooth muscle was recorded on a polygraph (U-228 manufactured by NIPPON DENKI KAGAKU) via an isotonic transducer (TD-112S manufactured by Nihon Koden). Each test compound was incubated for 5 minutes before the addition of $3 \times 10^{-5}$M of histamine hydrochloride (a product of Wako Pure Chemical Industries, Ltd.). The results are shown in Table 2.

TABLE 2

| | 5-Lipoxygenase-inhibiting action $IC_{50}$ (M) | Histamine antagonism $10^{-5}$ M (%) |
|---|---|---|
| Example 5 | $4.1 \times 10^{-7}$ | 65.4 |
| 34 | $1.5 \times 10^{-7}$ | 64.7 |
| 35 | $2.7 \times 10^{-7}$ | 67.9 |
| 43 | $1.1 \times 10^{-7}$ | 48.2 |

TEST EXAMPLE 4

TX synthesis-inhibiting action $TXA_2$ synthetase activity was measured by the use of a thromboxane synthetase kit (Funakoshi: Eldan Tech). That is, 0.97 mg of a human platelet microsome fraction was suspended in 1 m of a 50 mM tris-0.1M sodium chloride buffer solution of pH 7.5, and the resulting suspension was ice-cooled. 0.1M of the suspension was placed in a sample tube and a test compound was added thereto. The resulting mixture was preincubated at 25° C. exactly for 3 minutes. Thereto was added 2μ of an ice-cooled acetone solution containing 0.05 mg/m of PGH$_2$, and the resulting mixture was incubated at 25° C. exactly for 3 minutes. 10μ of a 0.25 mM FeCl$_2$ solution was added to terminate the reaction. The resulting mixture was allowed to stand at room temperature for 15 minutes and then subjected to centrifugation at 1,000 G at 4° C. for 10 minutes. The TXB$_2$ content contained in the supernatant was measured by RIA (thromboxanes B$_2$[3H] RIA Kit: NEN Research Products). The test compound was dissolved in DMSO or distilled water before use. The test was performed in triplicate or quadruplicate assays. The results are shown in Table 3.

TABLE 3

|  | 5-Lipoxygenase-inhibiting action IC$_{50}$ (M) | Thromboxane synthesis inhibiting-action $3 \times 10^{-6}$ M (%) |
|---|---|---|
| Example 15 | $3.0 \times 10^{-7}$ | 73.2 |
| 43 | $1.1 \times 10^{-7}$ | 75.6 |
| 44 | $3.9 \times 10^{06}$ | 61.8 |

As is clear from the above test results, the compound of the present invention has a 5-lipoxygenase-inhibiting action, a TXA$_2$ synthetase-inhibiting action, a histamine antagonism and a cell membrane-stabilizing action for histamine-release from mast cells, and is expected to find application as a drug for allergoses treatment (an antiallergic agent).

In using the present compound as an anti-allergic agent for treatment of allergosis patients, the compound can be administered to the patients orally, parenterally (intravenous injection, subcutaneous injection, intramuscular injection, etc.) per rectum or topically (inhalation). The dose of administration can be varied depending upon the symptom, age, weight, sex, etc. of patient, diagnosis of doctor, the administration route, etc., but the appropriate dose is generally 0.1-9 mg/kg of weight/day, preferably 2-6 mg/kg of weight/day.

In administration of the compound of the present invention, the compound can be mixed with a pharmaceutically acceptable carrier or diluent to formulate into various dosage forms such as tablets, capsules, sugar-coated tablets, granules, powder, syrup, injection, suppositories, inhalant and the like.

The usable carrier or diluent includes lactose, starch, cellulose crystals, calcium carbonate, mannitol, maltose, polyvinylpyrrolidone starch, hydroxypropyl cellulose, ethyl cellulose, carboxymethyl cellulose, gum arabic, etc.

The present invention is hereinafter described more specifically by way of Examples, Reference Examples and Preparation Examples.

REFERENCE EXAMPLE 1

Synthesis of 3,5-diacetoxy-2-naphtoic acid

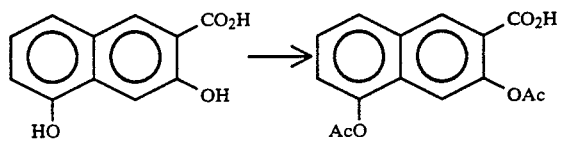

In 30 m of pyridine were dissolved 1.14 g (5.6 mM) of 3,5-dihydroxy-2-naphtoic acid and 1.4 g (13.9 mM) of acetic anhydride. The resulting solution was stirred at room temperature overnight to give rise to a reaction. After the completion of the reaction, the solvent was removed under reduced pressure. The residue was dissolved in 100 ml of ethyl acetate. The resulting solution was washed with 50 ml of a saturated potassium hydrogensulfate solution and two 50 ml portions of a saturated aqueous sodium chloride solution and dried over anhydrous sodium sulfate. The solvent was removed by distillation. The residue was purified by silica gel chromatography (elutant: 5% methanol-dichloromethane) to obtain 1.5 g of the title compound at a yield of 93%.

REFERENCE EXAMPLE 2

Synthesis of 3-hydroxy-5-(3-pyridyloxy)-2-naphtoic acid

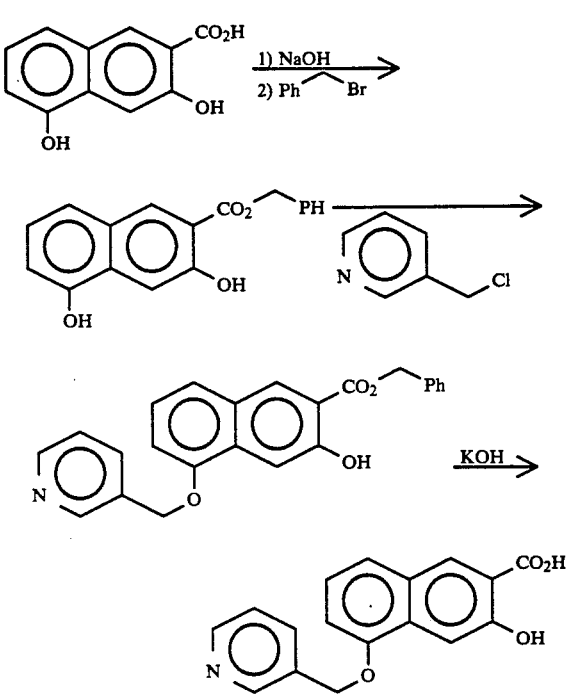

2-1 Synthesis of benzyl 3,5-dihydroxy-2-naphtoate 3 g (14.7 mM) of 3,5-dihydroxynaphthoic acid was dissolved in 100 ml of ethanol. Thereto was added mg (1.47 mM) of sodium hydroxide. The mixture was stirred at room temperature for 3 hours to give rise to a reaction. After the completion of the reaction, the solvent was removed under reduced pressure. To the reside were added 100 ml of acetonitrile, 2.57 g (14.7 mM) of benzyl bromide and 500 mg (14.7 mM) of tetra-n-butylammonium hydrogensulfate. The resulting mixture was refluxed overnight with heating, to give rise to a reaction. After the completion of the reaction, the solvent was removed under reduced pressure. The residue was dissolved in ethyl acetate. The resulting solution was washed with a saturated aqueous sodium chloride solution and dried over anhydrous sodium sulfate. The solvent was removed by distillation. The residue was purified by silica gel chromatography to obtain 4.2 g of the title compound at a yield of 97%.

2-2 Synthesis of benzyl 3-hydroxy-5-(3-pyridyloxy)-2-naphtoate 500 mg (1.7 mM) of benzyl 3,5-dihydroxynaphtoate was dissolved in 100 ml of acetonitrile. Thereto were added 434 mg (3.4 mM) of 3-picolyl chloride and 235 mg (1.7 mM) of potassium carbonate. The resulting mixture was stirred for 7 hours to give rise to a reaction.

After the completion of the reaction, the solvent was removed under reduced pressure. The reside was dissolved in ethyl acetate. The resulting solution was washed with a saturated aqueous sodium chloride solution and dried over anhydrous sodium sulfate. The solvent was removed by distillation. The residue was purified by silica gel chromatography to obtain 480 mg of the title compound at a yield of 73%.

2-3 3-Hydroxy-5-(3-pyridyloxy)2-naphthoic acid 500 mg (1.3 mM) of the compound obtained above was dissolved in 50 ml of a 10:1 mixture of ethanol and water. To the resulting solution was added 72.8 mg (2.6 mM) of potassium hydroxide. The resulting mixture was refluxed for 2 hours with heating, to give rise to a reaction. After the completion of the reaction, the reaction mixture was neutralized with 5% hydrochloric acid. The solvent was removed under reduced pressure. The residue was placed in water, and the resulting crystals were collected by filtration to obtain 350 mg of the title compound at a yield of 90%.

REFERENCE EXAMPLE 3

Synthesis of 3,5-dimethoxy-2-naphtoic acid

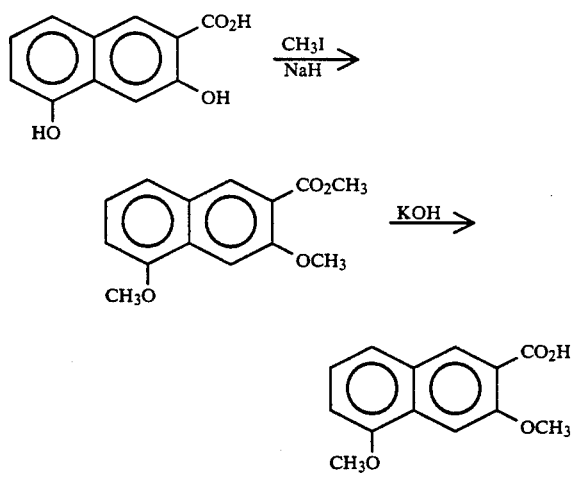

3-1 Methyl 3,5-dimethoxy-2-naphthoate 2 g (9.8 mM) of 3,5-dihydroxy-2-naphthoate was dissolved in 50 ml of anhydrous dimethylformamide. Thereto was added 1.5 g (29.4 mM) of sodium hydride. The resulting mixture was stirred for 30 minutes. Then, 4.9 g (34.3 mM) of methyl iodide was added and stirring was conducted overnight to give rise to a reaction. After the completion of the reaction, water was added to the reaction mixture. The solvent was removed under reduced pressure. The residue was dissolved in ethyl acetate. The resulting solution was washed with a saturated aqueous sodium chloride solution and dried over anhydrous sodium sulfate. The solvent was removed by distillation. The residue was purified by silica gel chromatography to obtain 2.35 g of the title compound at a yield of 98%.

3-2 3,5-Dimethoxy-2-naphthoic acid

The title compound was obtained according to the method of Reference Example 2-3, at a yield of 90%.

REFERENCE EXAMPLE 4

Synthesis of 5-(2-thienylmethylthio)pentamine

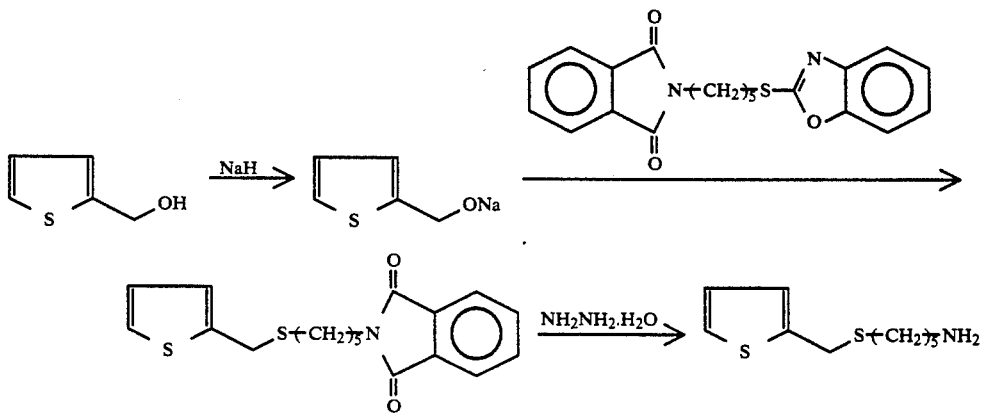

2 g (17.5 mM) of 2-thiophenemethanol was dissolved in 15 ml of dimethylformamide. Thereto was added 800 mg (20 mM) of 60% sodium hydride in a nitrogen stream with ice cooling, and the mixture was stirred. When hydrogen generation was over, thereto was dropwise added a solution of 6.5 g of N-{5-(2-benzoxazolyl-thio)pentyl}phthalimide in 30 ml of DMF. The resulting mixture was stirred for 3 hours with ice cooling and for 60 hours at room temperature to give rise to a reaction. After the completion of the reaction, the reaction mixture was placed in ice water. Extraction with benzene was conducted. The benzene layer was washed with water and a saturated aqueous sodium chloride solution in this order and dried over anhydrous sodium sulfate. The solvent was removed by distillation. The residue was purified by silica gel chromatography to obtain 4.84 g of N-{5-(2-thienylmethylthio)pentylphthalimide at a yield of 80%.

2 g (5.79 mM) of the phthalimide compound was dissolved in 30 ml of methanol. Thereto was added 435 mg (8.7 mM) of hydrazine hydrate, and the mixture was refluxed for 1 hour with heating. After cooling, the resulting crystals were collected by filtration and washed with ether. The filtrate and the washings were combined. The solvent was removed by distillation. The residue was mixed with ether. This procedure was repeated until no precipitate was formed, whereby 1.18 g of the title compound, i.e. 5-(2-thienylmethylthio)pentamine was obtained at a yield of 95%.

NMR($\delta$, CDCl$_3$); 1.40–1.45(2H, m), 1.56–1.61(2H, m), 1.71(2H, s), 2.50(2H, t, J=6Hz), 2.69(2H, t, J=7Hz), 3.92(2H, s), 6.91–6.93(2H, m), 7.20(1H, dd, J=5 Hz, 2 Hz)

REFERENCE EXAMPLE 5

Synthesis of 3-(2-thienylmethylthio)propaneamine

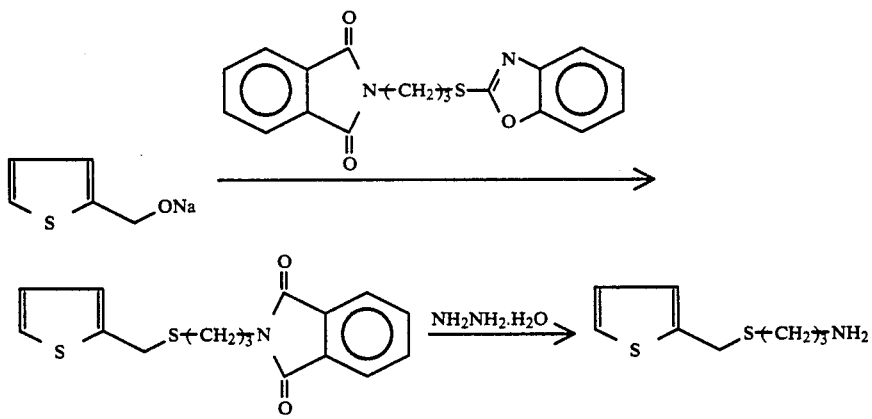

The same reaction as in Reference Example 4 was repeated except that the N-[5-(2-benzoxazolylthio)pentyl]phthalimide was replaced by N-[3-(2-benzoxazolylthio)propyl]phthalimide, to obtain the title compound at a yield of 78%.

NMR(δ, DCDl₃); 1.41(2H, br4-s), 1.72(2H, t, J=6 Hz), 2.56(2H, t, J=6 Hz), 2.78(2H, t, J=6 Hz), 3.93(2H, s), 6.91–6.93(2H, m), 7.20(1H, dd, J=6 Hz, 2 Hz)

REFERENCE EXAMPLE 6

Synthesis of 1-(2-aminoethyl)-4-benzhydrylthiopiperidine 278 mg (1.39 mM) of benzhydrylthiol was dissolved in 10 ml of dimethylformamide. Thereto was added 60.7 mg (1.39 mM) of 60% sodium hydride in a nitrogen stream, with ice cooling. When hydrogen generation was over, there was dropwise added a solution of 262 mg (1.39 mM) of N-acetyl-4-methanesulfonyloxypiperidine in 10 ml of dimethylformamide. The resulting mixture was stirred at room temperature for 5 hours to give rise to a reaction. After a completion of the reaction, the solvent was removed under reduced pressure. The residue was subjected to extraction with ethyl acetate, and the extract was washed with water and a saturated aqueous sodium chloride solution in this order and dried over anhydrous sodium sulfate. The solvent was removed by distillation. The residue was purified by silica gel chromatography to obtain 230 mg of N-acetyl-4-benzhydrylthiopiperidine at a yield of 60%.

200 mg (0.81 mM) of the compound was dissolved in 10 ml of methanol. Thereto was added a solution of 40

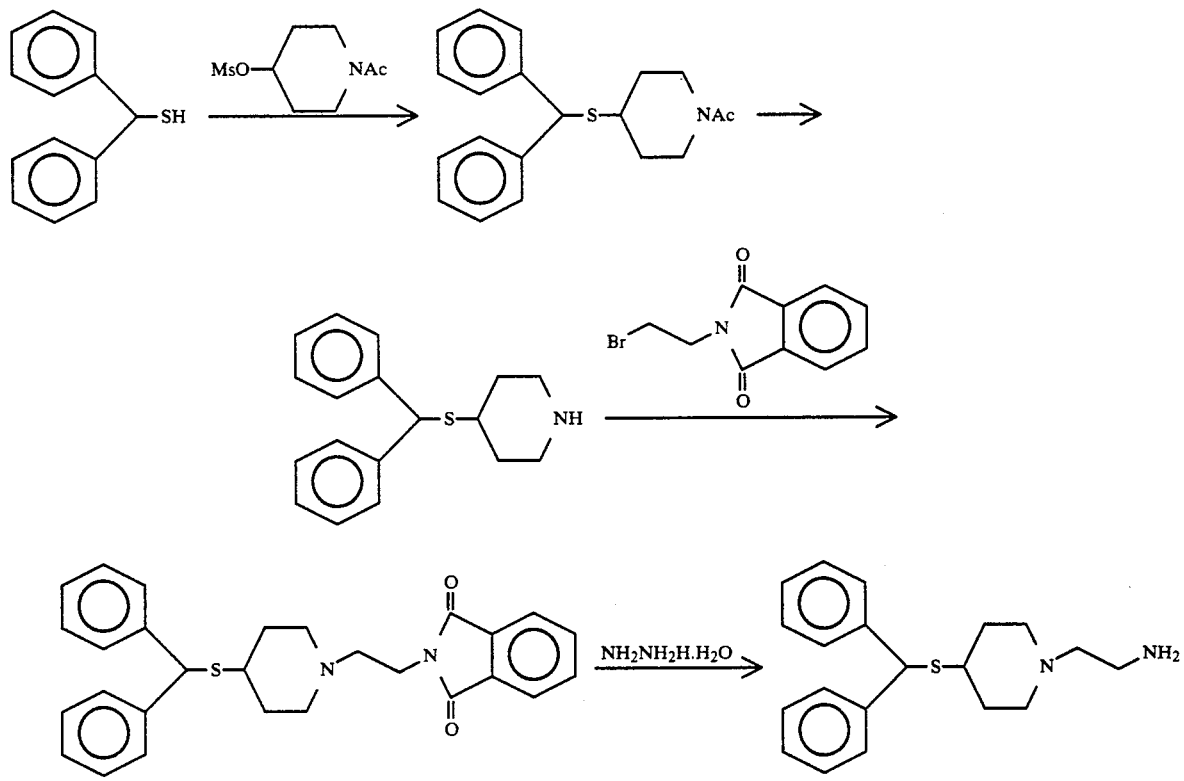

mg (1.0 mM) of sodium hydroxide in 10 ml of water. The mixture was refluxed for 10 hours with heating to give rise to a reaction. After the completion of the reaction, the solvent was removed under reduced pressure. The residue was subjected to extraction with chloroform. The extract was washed with water and a saturated aqueous sodium chloride solution in this order and dried over anhydrous sodium sulfate. The solvent was removed by distillation. The residue was purified by silica gel chromatography to obtain 225 mg of 4-benzhydrylthiopiperidine at a yield of 98%.

227 mg (0.8 mM) of the compound and 262 mg (1.4 mM) of N-(2-bromoethyl)phthalimide were dissolved in 15 ml of methyl ethyl ketone. Thereto were added 220 mg (1.6 mM) of anhydrous potassium carbonate and 226 mg (1.5 mM) of sodium iodide. The mixture was refluxed for 8 hours with heating, to give rise to a reaction. After the completion of the reaction, the solvent was removed under reduced pressure. The residue was subjected to extraction with chloroform. The extract was washed with water and a saturated aqueous sodium chloride solution in this order and dried over anhydrous sodium sulfate. The solvent was removed by distillation. The residue was purified by silica gel chromatography to obtain 237 mg of N-[2-(4-benzhydrylthiopiperidinyl)ethyl]phthalimide at a yield of 65%.

The above phthalimide was treated with hydrazine hydrate in the same manner as in Reference Example 4, to obtain the title compound, i.e. 1-(2-aminoethyl)-4-benzhydrylthiopiperidine at a yield of 92%.

NMR(δ, CDCl$_3$); 1.57–1.70(4H, m), 1.84–1.90(2H, m), 1.95–2.02(2H, m), 2.34(2H, t, J=6 Hz), 2.44–2.51(1H, m), 2.72–2.80(2H, m), 5.22(1H, s), 7.19–7.33(6H, m), 7.41–7.44(4H, m)

REFERENCE EXAMPLE 7

Synthesis of N-(2-aminoethyl)-N'-[2-(2-thienylmethylthio)ethyl)piperazine

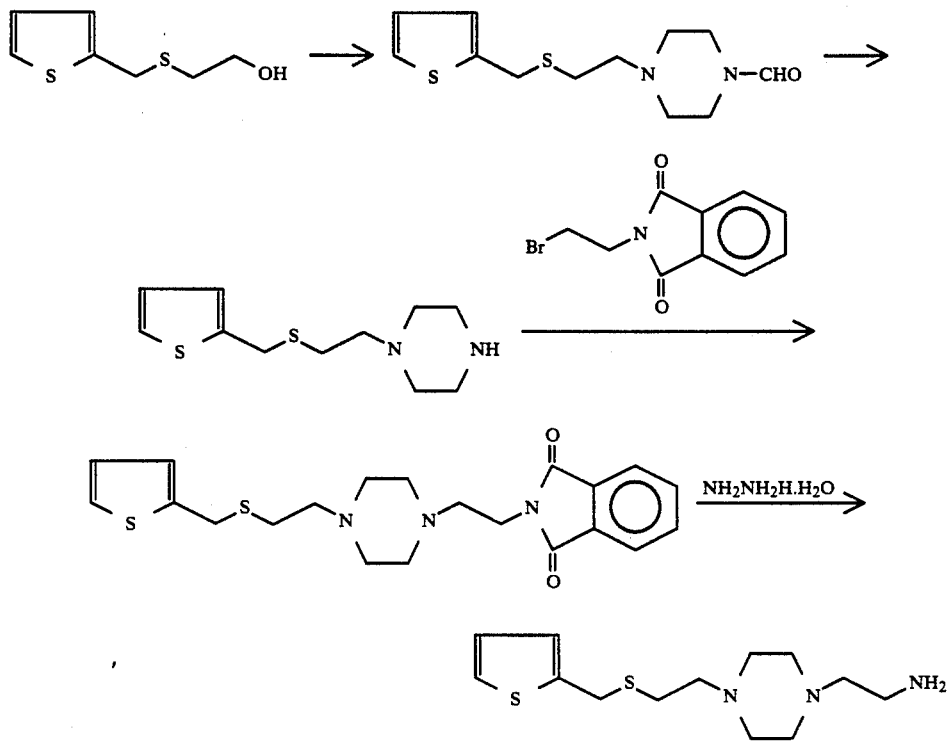

In 20 ml of ethyl acetate were dissolved 925 mg (6.3 mM) of 2-(2-thienylmethylthio)ethanol and 765 mg (7.6 mM) of triethylamine. Thereto was dropwise added, with ice cooling, a solution of 800 mg (7.0 mM) of methanesulfonyl chloride in 10 ml of ethyl acetate. The mixture was stirred at room temperature for 1 hour to give rise to a reaction. After the completion of the reaction, the insolubles were removed by filtration. The filtrate was mixed with 2.15 g (19.0 m) of formylpiperazine. The mixture was refluxed for 7 hours with heating to give rise to a reaction. After the completion of the reaction, extraction with ethyl acetate was conducted. The extract was washed with water and a saturated aqueous sodium chloride solution in this order and dried over anhydrous sodium sulfate. The solvent was removed by distillation. The residue was purified by silica gel chromatography to obtain 1.27 g of N-formyl-N'-[2-(2-thienylmethylthio)ethyl]piperazine at a yield of 75%.

1 g (3.7 mM) of N-formyl-N'-[2-(2-thienylmethylthio)ethyl]piperazine was dissolved in 10 ml of methanol. Thereto was added a solution of 178 mg (4.4 mM) of sodium hydroxide in 10 ml of water. The mixture was refluxed for 10 hours with heating, to give rise to a reaction After the completion of the reaction, the solvent was removed under reduced pressure. The residue was subjected to extraction with chloroform. The extract was washed with water and a saturated aqueous sodium chloride solution in this order and dried over anhydrous sodium sulfate. The solvent was removed by distillation. The residue was purified by silica gel chromatography to obtain 800 mg of N-[2-(2-thienylmethylthio)ethyl]piperazine at a yield of 89%.

The N-[2-(2-thienylmethylthio)ethyl]piperazine was treated in the same manner as in Reference Example 6 to obtain the title compound, i.e. N-(2-aminoethyl)-N'-[2-(2-thienylmethylthio)ethyl]piperazine at a yield of 75%.

NMR(δ, CDCl$_3$); 1.63(2H, s), 2.40-2.6(14H, m), 2.77(2H, t, J=6 Hz), 3.96(2H, s), 6.90-6.92(2H, m), 7.20(1H, d, J-3 Hz)

REFERENCE EXAMPLE 8

Synthesis of 2-[N-methyl-N'[2-(2-thienylmethylthio)ethyl]amino]ethaneamine

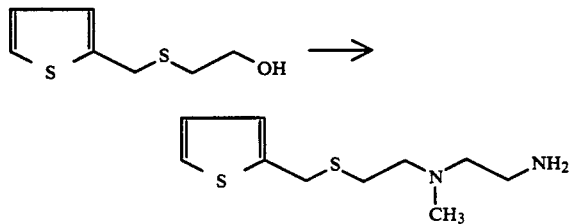

2-[N-methyl-N'[2-(2-thienylmethylthio)ethylamino]ethaneamine was obtained from 2-(2-thienylmethylthio)ethanol according to Reference Example 7.

NMR(δ, CDCl$_3$); 1.54(2H, br-s), 2.20(3H, s), 2.41(2H, t, J=6 Hz), 2.57-2.60(4H, m), 2.74(2H, t, J=6 Hz), 3.95(2H, s), 6.87-6.93(2H, m), 7.20(1H, dd, J-3 Hz, 1 Hz)

EXAMPLE 1

Synthesis of N-[5-(2-thienylmethylthio)pentyl]-3,5-diacetoxy-2-naphthamide

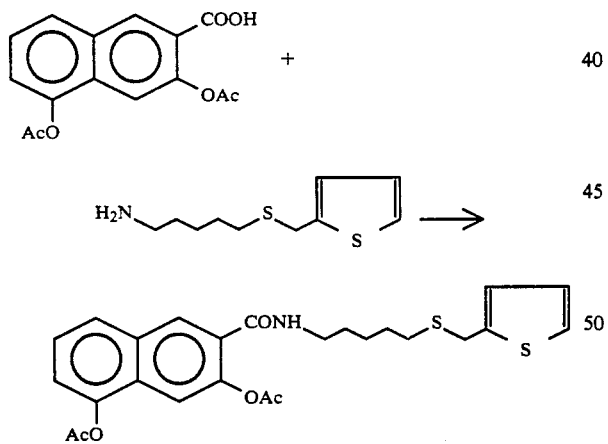

260 mg (0.9 mM) of 3,5-diacetoxy-2-naphthoic acid was dissolved in 20 ml of dichloromethane. Thereto was added 161 mg (1.35 mM) of thionyl chloride. The mixture was refluxed for 1 hour with heating. The solvent was removed by distillation. The residue was dissolved in 20 ml of dichloromethane. Thereto were added 159 mg (2.7 mM) of sodium carbonate and 15 ml of water. To the resulting mixture was added 194 mg (0.9 mM) of 5-(2-thienylmethylthio)-pentaneamine with ice cooling, and stirring was conducted at room temperature for 1 hour to give rise to a reaction. After the completion of the reaction, extraction with dichloromethane was conducted. The extract was washed with water and a saturated aqueous sodium chloride solution in this order, and dried over anhydrous sodium sulfate. The solvent was removed by distillation. The residue was purified by silica gel chromatography to obtain 306 mg of the title compound at a yield of 70%:

IR (cm$^{-1}$, KBr): 1650, 1770

Mass spectrometry Calculated: 485.1330 as C$_{25}$H$_{27}$O$_5$NS$_2$ Observed: 485.1312

NMR(δ, CDCl$_3$): 1.45-1.53(2H, m), 1.54-1.69(2H, m), 2.37(3H, s), 2.46(3H, s), 2.53(2H, t, J=6 Hz), 3.44(2H, dt, J=6 Hz,6 Hz), 3.92(2H, s), 6.26(1H, br-s), 6.87-6.92(2H, m), 7.19(1H, dd, J=5 Hz, 2 Hz), 7.35(1H, d, J=9 Hz), 7.51(1H, dd, J=6 Hz, 6 Hz), 7.59(1H, s), 7.78(1H, d, J=9 Hz), 8.22(1H, s)

EXAMPLES 2 AND 3

Reactions between 3,5-diacetoxy-2-naphthoic acid and amine compound were conducted in the same manner as in Example 1 to obtain the following amide derivatives.

EXAMPLE 2

N-[3-(2-thienylmethylthio)propyl]-3,5-diacetoxy-2-naphthamide

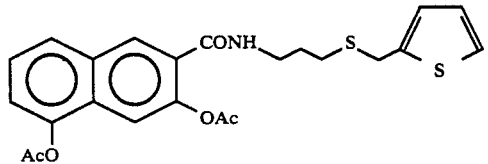

Yield: 86%

IR (cm$^{-1}$, CHCl$_3$): 1600, 1770

Mass spectrometry Calculated: 457.1016 as C$_{23}$H$_{23}$O$_5$NS$_2$ Observed: 457.1009

NMR(δ, CDCl$_3$): 1.89(2H, t, J=6 Hz), 2.36(3H, s), 2.46(3H, s), 2.61(2H, t, J=6 Hz), 3.53(2H, dt, J=6 Hz, 6 Hz), 3.95(2H, s), 6.38(1H, br-s), 6.85-6.88(1H, m), 7.16(1H, dd, J=5 Hz, 2 Hz), 7.36(1H, d, J=8 Hz), 7.51(1H, dd, J=8 Hz, 8 Hz), 7.59(1H, s), 7.77(1H, d, J=8 Hz), 8.17(1H, s)

EXAMPLE 3

N-[4-[2-(2-thienylmethylthio)piperazyl]-3,5-diacetoxy-2-naphthamide

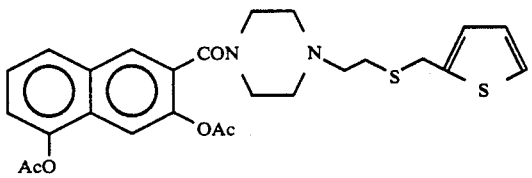

Yield: 75%

IR(cm$^{-1}$, CHCl$_3$): 1630, 1770

Mass spectrometry Calculated: 512.1438 as C$_{26}$H$_{28}$O$_5$N$_2$S$_2$ Observed: 512.1435

NMR(δ, CDCl$_3$): 2.94-2.61(8H, m), 2.32(3H, s), 2.46(3H, s), 3.36(2H, br-s), 3.81(2H, br-s), 3.96(2H, s), 6.90-6.93(2H, m), 7.20 (1H, dd, J-4 Hz, 2 Hz), 7.34 (1H, d, J=8 Hz), 7.51(1H, dd, J=8 Hz, 8HZ), 7.66(1H, s), 7.73(1H, d, J=8 Hz), 7.81(1H, s)

EXAMPLE 4

Synthesis of
N-[2-[4-(thienylmethylthio)ethyl-1-piperazinyl]ethyl]-
5-acetoxy-3-hydroxy-2-naphthamide

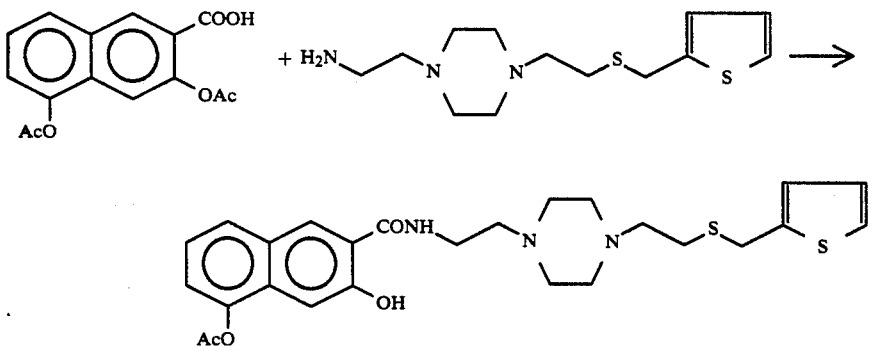

375 mg (1.3 mM) of 3,5-diacetoxy-2-naphthoic acid was dissolved in 20 ml of dichloromethane. Thereto was added 238 mg (2.0 mM) of thionyl chloride. The mixture was refluxed for 1 hour with heating. The solvent was removed by distillation. The residue was dissovled in 20 ml of dichloromethane. The solution was dropwise added to a mixed solution consisting of 1.33 mg (1.3 mM) of triethylamine, 349 mg (1.3 mM) of N-(2-aminoethyl)-N'-[2-(2-thienylmethylthio)ethyl]piperazine and 20 ml of dichloromethane. Stirring was conducted at room temperature for 1 hour to give rise to a reaction. After the completion of the reaction, extraction with dichloromethane was effected. The extract was washed with water and a saturated aqueous sodium chloride solution in this order, and dried over anhydrous sodium sulfate. The solvent was removed by distillation. The residue was purified by silica gel chromatography to obtain 467 mg of the title compound at a yield of 70%.

IR (cm$^{-1}$, CHCl$_3$): 1660, 1770

Mass spectrometry Calculated: 513.1755 as C$_{26}$H$_{31}$N$_3$O$_4$S$_2$ Observed: 513.1746

NMR($\delta$, CDCl$_3$): 2.54–2.70(12H, m), 2.44(3H, s), 3.57(2H, t, J=6 Hz), 3.96(2H, s), 6.90–6.93(2H, m), 7.20(1H, dd, J=3 Hz, 2 Hz), 7.25–7.28(3H, m), 7.53(1H, br-s), 7.61(1H, dd, J-5 Hz, 2 Hz), 7.98(1H, s)

EXAMPLES 5 TO 19

Reactions between carboxylic acid compound and amine compound were conducted in the same manner as in Example 4 to obtain the following amide derivatives.

EXAMPLE 5

N-[2-[4-(benzhydryloxy)piperidino]ethyl]-5-acetoxy-3-hydroxy-2-naphthamide

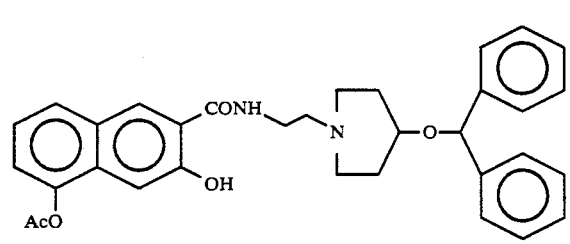

Yield: 73%

IR (cm$^{-1}$, KBr): 1660, 1770

Mass spectrometry Calculated: 538.2467 as C$_{33}$H$_{34}$O$_5$N$_2$ Observed: 538.2452

NMR($\delta$, CDCl$_3$): 1.83–1.86(2H, m), 1.99–2.02(2H, m), 2.43(3H, s), 2.58–2.60(2H, m), 2.80(2H, t, J=6 Hz), 2.90–2.96(2H, m), 3.58–3.65(4H, m), 5.50(1H, s), 7.21–7.34(13H, m), 7.65(1H, dd, J=6 Hz, 2 Hz), 8.15(1H, s)

EXAMPLE 6

N-[2-[methyl-[2-(2-thienylmethylthio)ethylamino]ethyl]-5-acetoxy-4-hydroxy-2-naphthamide

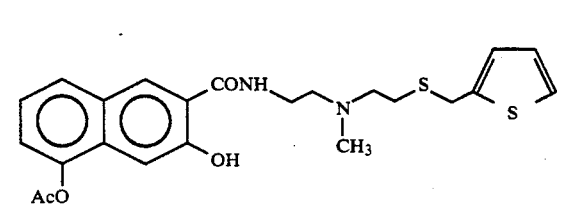

Yield: 70%

IR (cm$^{-1}$, CHCl$_3$): 1670, 1780

Mass spectrometry Calculated: 458.1333 as C$_{23}$H$_{26}$O$_4$N$_2$S$_2$ Observed: 458.1318

NMR($\delta$, CDCl$_3$): 2.31(3H, s), 2.45(3H, s), 2.62–2.71(4H, m), 2.74–2.77(2H, m), 3.55(2H, dt, J=6 HZ), 3.94(2H, s), 6.83–6.87(2H, m), 7.15(1H, dd, J=6 Hz, 3 HZ), 7.24(2H, d, J-5 Hz), 7.29(1H, s), 7.54(1H, dd, J=5 Hz, 5 Hz), 7.78(1H, br-s), 8.28(1H, s)

EXAMPLE 7

N-[2-[4-(benzhydrylthio)piperidino]ethyl]-5-acetoxy-3-hydroxy-2-naphthamide

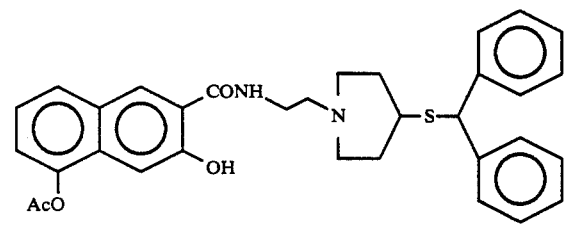

Yield: 55%

IR (cm$^{-1}$, CHCl$_3$): 1660, 1780

Mass spectrometry Calculated: 554.2239 as C$_{33}$H$_{34}$O$_4$N$_2$S Observed: 554.2245

NMR($\delta$, CDCl$_3$) 1.60–1.75(2H, m), 1.92–2.01(2H, m), 2.06–2.17(2H, m), 2.44(3H, s), 1.48–1.55(1H, m)

2.59(2H, 5, J=6 Hz), 2.84-2.88(2H, m), 2.51-3.54(2H, m), 5.25(1H, s), 7.20-7.34(10H, m), 7.42-7.45(3H, m), 7.64(1H, dd, J=9 Hz, 2 Hz), 7.94(1H, s)

EXAMPLE 8

N-[2-[4-(4-chlorophenylthio)piperidone]ethyl]-5-acetoxy-3-hydroxy-2-naphthamide

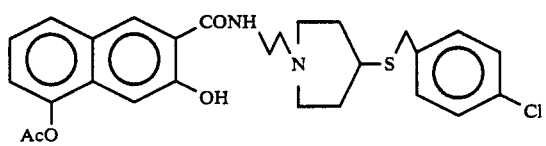

Yield: 77%
IR (cm⁻¹, CHCl₃): 1670, 1780
Mass spectrometry Calculated: 512.1536 as $C_{27}H_{29}O_4N_2SCl$ Observed: 512.1538

NMR(δ, CDCl₃): 1.63-1.69(2H, m), 1.95-2.00(2H, m), 2.14-2.21(2H, m), 2.45(3H, s), 2.55-2.62 (3H, m), 2.88-2.94(2H, m), 3.56(2H, dt, J=6 Hz, 6 Hz), 3.73(2H, s), 7.24-7.28(5H, m) 7.31(1H, s), 7.41(1H, br-s), 7.67(1H, d, J=7 Hz), 7.97(1H, s)

EXAMPLE 9

N-[2-14-(benzhydrylthio)ethyl-1-piperazinyl]ethyl]-5-acetoxy-3-hydroxy-2-naphthamide

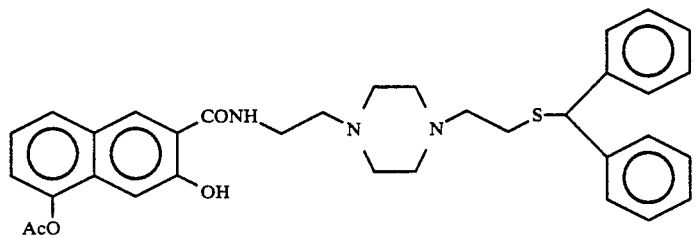

Yield: 74%
IR (cm⁻¹, CHCl₃): 1660, 1770
Mass spectrometry Calculated: 583.2504 as $C_{34}H_{37}O_4N_3S$ Observed: 583.2514

NMR (δ, CDCl₃) 2.44-2.60(12H, m), 2.66(2H, t, J=6 Hz), 3.55(2H, dt, J=5 Hz, 5 Hz), 5.22(1H, s), 7.19-7.33(8H, m), 7.40-7.44(5H, m), 7.65(1H, d, J=5 Hz), 7.95(1H, s)

EXAMPLE 10

N-[2-[4-(2-pyridylmethylthio)ethyl-1-piperazinyl]ethyl]-5-acetoxy-3-hydroxy-2-naphthamide

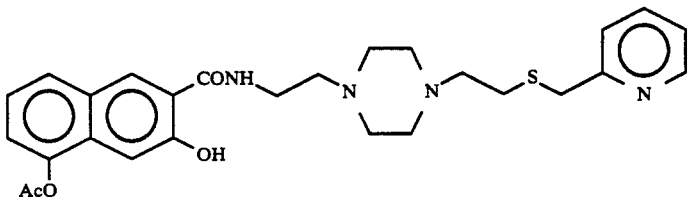

Yield: 66%
IR (cm⁻¹, CHCl₃): 1660, 1770
Mass spectrometry Calculated: 508.2144 as $C_{27}H_{32}N_4O_4S$ Observed: 508.2173

(NMR(δ, CDCl₃): 2.44(3H, s), 2.53-2.68(14H, m) 3.55(2H, dt, J=6 Hz, 6 Hz), 3.87(2H, s), 7.16(1H, dd, J=6 Hz, 6 Hz), 7.24-7.31(3H, m), 7.38(1H, d, J=8 Hz), 7.49(1H, br-s), 7.62-7.68(2H, m), 7.98(1H, s), 8.51(1H, d, J-5 Hz)

EXAMPLE 11

N-[2-[4-(2-pyridylphenylmethylthio)ethyl-1-piperazinyl]ethyl]-5-acetoxy-3-hydroxynaphthamide

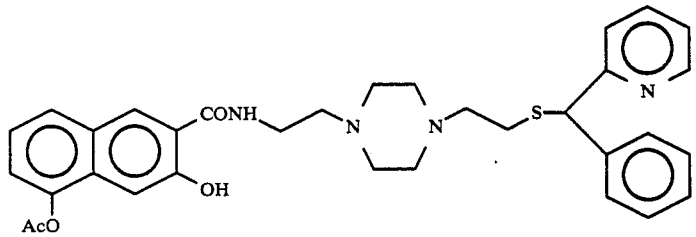

Yield: 67%
IR (cm⁻¹, CHCl₃): 1660, 1780
Mass spectrometry Calculated: 572.2457 as $C_{32}H_{36}O_4N_4S$ Observed: 572.2477

NMR(δ, CDCl₃) 2.44(3H, s), 2.35-2.79(14H, m), 2.77(2H, t, J=6 Hz), 5.33(1H, s), 7.14(1H, ddd, J=7 Hz 5 Hz, 2 Hz), 7.24-7.35(6H, m), 7.44(1H, dd, J=6 Hz, 1Hz), 7.48-7.50(2H, m), 7.62(1H, ddd, J=7 Hz, 7 Hz, 2 Hz), 7.69(1H, d, J=5 Hz), 7.80(1H, br-s), 8.01(1H, dd, J=5 Hz, 2 Hz)

EXAMPLE 12

N-[2-[4-(4-chlorophenylmethylthio)ethyl-1-piperazinyl]ethyl]-5-acetoxy-3-hydroxy-2-naphthamide

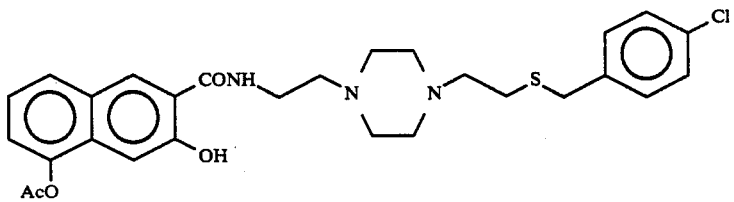

Yield: 65%
IR (cm$^{-1}$, CHCl$_3$): 1660, 1770
Mass spectrometry Calculated: 541.800 as C$_{28}$H$_{32}$O$_4$N$_3$SCl Observed: 541.1780
NMR(δ, CDCl$_3$): 2.45(3H, s), 2.46–2.64(12H, m), 2.72(2H, t, J=6 Hz), 3.60(2H, dt, J=6 Hz, 6 Hz), 3.70(2H, s), 7.23–7.29(6H, m), 7.31(1H, s), 7.54(1H, br-s), 7.68(1H, s), 8.03(1H, s)

EXAMPLE 13

N-[2-[4-(5-chloro-2-thienylmethylthio)ethyl-1-piperazinyl]ethyl]-5-acetoxy-3-hydroxy-2-naphthamide

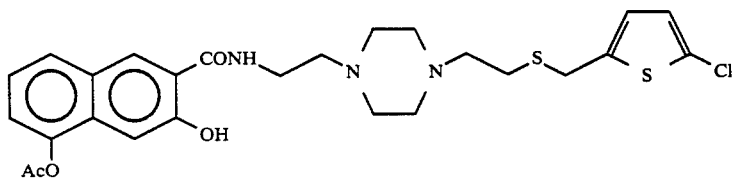

Yield: 62%
IR (cm$^{-1}$, CHCl$_3$): 1680, 1780
Mass spectrometry Calculated: 547.1366 as C$_{26}$H$_{30}$O$_4$N$_3$S$_2$Cl Observed: 547.1379
NMR(δ, CDCl$_3$): 2.45(3H, s), 2.55–2.70(12H, m) 2.68(2H, t, J=6 Hz), 2.68(2H, t, J=6 Hz), 3.58(2H, dt, J=6 Hz, 6 Hz), 3.85(2H, s), 6.70(2H, m), 7.25–7.26(2H, m), 7.29(1H, s), 2.40(1H, br-s), 7.64(1H, d, J=7 Hz), 7.96(1H, s)

EXAMPLE 14

N-[2-[4-[(4-chlorophenyl)-phenylmethylthio]ethyl-1-piperazinyl]ethyl]-5-acetoxy-3-hydroxy-2-naphthamide

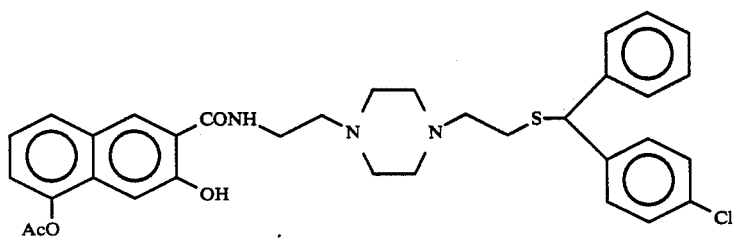

Yield: 53%
IR (cm$^{-1}$, CHCl$_3$): 1670, 1780
Mass spectrometry Calculated: 617.2114 as C$_{34}$H$_{36}$O$_4$N$_4$SCl Observed: 617.2087
NMR(δ, CDCl$_3$): 2.45(3H, s), 2.44–2.70(12H, m), 2.68(2H, t, J=6 Hz), 3.57(2H, dt, J=6 Hz, 6 Hz), 5.19(1H, s), 7.23–7.38(13H, m), 7.66(1H, d, J=7 Hz), 7.98(1H, s)

EXAMPLE 15

N-[2-[4-[(4-chlorophenyl)-4-pyridylmethylethyl]-5-acetoxy-3-hydroxy-2-naphthamide

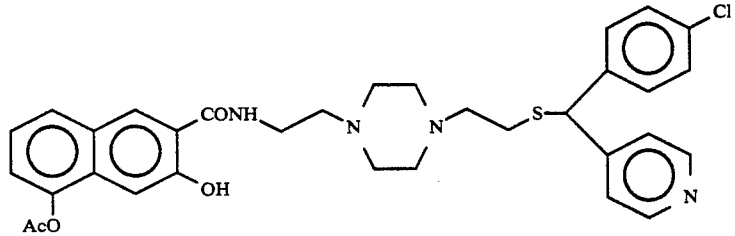

Yield: 58%
IR(cm$^{-1}$, CHCl$_3$): 1670, 1780
Mass spectrometry Calculated: 618.2066 as C$_{33}$H$_{35}$O$_4$N$_3$SCl Observed: 618.2038
NMR(δ, CDCl$_3$): 2.45(3H, s), 2.51–2.78(12H, m), 2.76(2H, t, J=6 Hz), 3.63(2H, dt, J=6 Hz, 6 Hz), 5.14(1H, s), 7.25–7.32(9H, m), 7.69(2H, d, J=8HZ), 8.10(1H, br-s), 8.56(2H, dd, J=5 Hz, 2 Hz)

EXAMPLE 16

N-[2-[4-(4-chlorodiphenylmethylthio)ethyl-1-piperazinyl]ethyl]-5-acetoxy-3-hydroxy-2-naphthamide

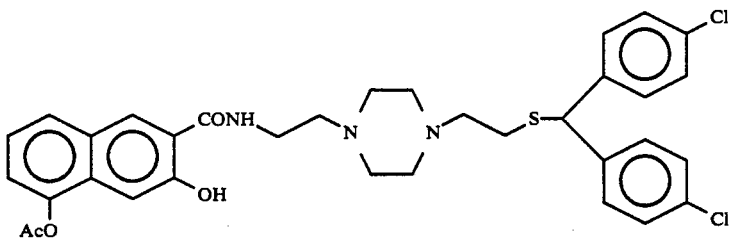

Yield: 70%
IR(cm⁻¹, CHCl₃): 1670, 1780

Mass spectrometry Calculated: 651.1725 as C₃₄H₃₅O₄N₃S₂Cl₂ Observed: 651.1733

NMR(δ, CDCl₃): 2.45(3H, s), 2.45–2.68(12H, m), 2.70(2H, t, J=6 Hz), 3.59(2H, dt, J=6 Hz, 6 Hz), 5.16(1H, s), 7.20–7.40(11H, m), 7.45(1H, br-s), 7.70(1H, d, J=6 Hz), 7.99(1H, s)

EXAMPLE 17

N-[2-[4-[2-(2-thienyl)ethyl-1-piperazinyl]ethyl-5-acetoxy-3-hydroxy-2-naphthamide

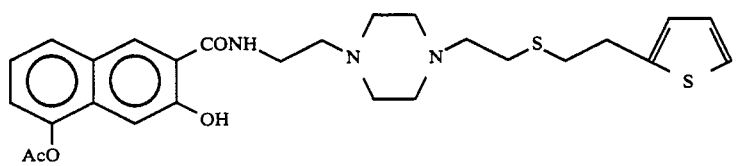

Yield: 72%
IR(cm⁻¹, CHCl₃): 1670, 1780
Mass spectrometry Calculated: 527.1911 as C₂₇H₃₃O₄N₃S₂ Observed: 527.1889

NMR(δ, CDCl₃) 2.45(3H, s), 2.60–2.72(14H, m), 2.85(2H, t, J=7 Hz), 3.12 (2H, t, J=7 Hz), 3.59(2H, dt, J=6 Hz, 6 Hz), 6.85(1H, dd, J=3 Hz, 1 Hz), 6.92–6.95(1H, m) 7.14(1H, dd, J=6 Hz, 2 Hz), 7.24–7.28(1H, m), 7.31(1H, s), 7.46(1H, br-s), 7.67(1H, d, J=7 Hz), 8.00(1H, s)

EXAMPLE 18

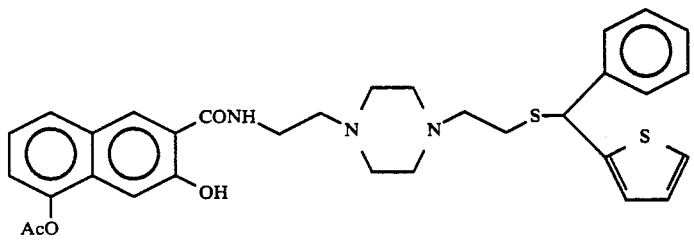

N-2-[4-(2-thienyl-phenylmethylthio]ethyl-1-piperazinyl]ethyl-5-acetoxy-3-hydroxy-2-naphthamde Yield: 67%
IR(cm⁻¹, CHCl₃): 1670, 1780
Mass spectromety Calculated: 589.2068 as C₃₂H₃₅O₄N₃S₂ Observed: 589.2088

NMR(δ, CDCl₃) 2.45(3H, s), 2.47–2.70(12H, m), 2.68(2H, t, J=6 Hz), 3.58(2H, dt, J=6 Hz, 6 Hz), 5.43(1H, s), 6.90–6.96(2H, m), 7.21(1H, dd, J=5 Hz, 2 Hz), 7.21–7.36(4H, m), 7.31(1H, s), 7.33(1H, s), 7.41–7.47(3H, m), 7.66(1H, d, J=8 Hz), 7.98(1H, s)

EXAMPLE 19

N-[2-[4-(2-phenylmethylthio)ethyl-1-piperazinyl]-ethyl]-5-acetoxy-3-hydroxy-2-naphthamide

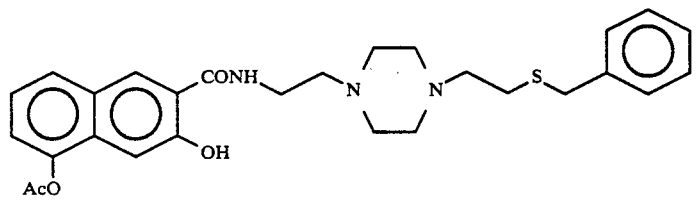

Yield: 67%
IR(cm⁻¹, KBr): 1670, 1780
Mass spectometry Calculated: 507.2190 as C₂₈H₃₃O₄N₃S Observed: 507.2187

NMR(δ, CDCl₃): 2.45(3H, s), 2.49–2.67(12H, m), 2.66(2H, t, J=5 Hz), 3.57(2H, t, J=5 Hz), 3.74(2H, s), 7.24–7.32(8H, m), 7.41(1H, br-s), 7.66(1H, d, J=8 Hz), 7.97(1H, s)

EXAMPLE 20

Synthesis of N-[2-[4-(2-thienylmethylthio)ethyl-1-piperazinyl]ethyl]-3,5-dihydroxy-2-naphthamide

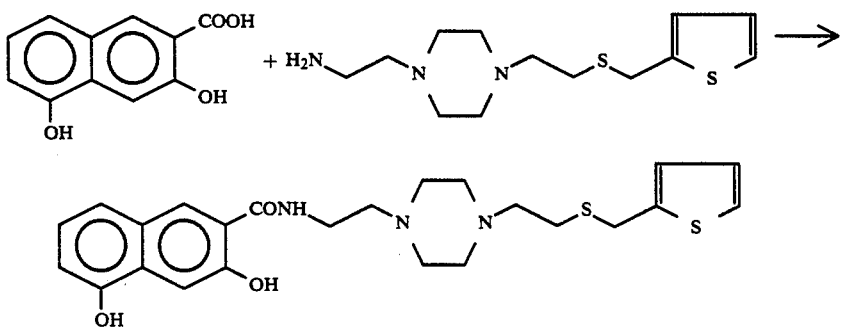

408 mg (2.0 mM) of 3,5-diacetoxy-2-naphthoic acid was dissovled in 20 ml of dichloromethane. Thereto were added 235 mg (2.0 mM) of N-hydroxysuccinimide and 422 mg (2.0 mM) of dicyclohexylcarbodiimide. The mixture was stirred at room temperature for 1 hour. Thereto was dropwise added a solution of 699 mg (2.0 mM) of N-(2-aminoethyl)-N-[2-(thienylmethylthio)ethyl]-piperazine in 20 ml of dichloromethane. Stirring was conducted at room temperature for 2 hours. After the completion of a reaction, extraction with dichloromethane was conducted. The extract was washed with a saturated aqueous sodium hydrogen-carbonate solution and a saturated aqueous sodium chloride solution two times, and dried over anhydrous sodium sulfate. The solvent was removed by distillation. The residue was mixed with 20 ml of acetonitrile, and the mixture was filtered. The filtrate was subjected to distillation to remove the solvent. The residue was purified by silica gel chromatogrpahy to obtain 632 mg of the title compound at a yield of 67%.

IR(cm$^{-1}$, CHCl$_3$): 1670

Mass spectrometry Calculated: 471.1650 as C$_{24}$H$_{29}$O$_3$N$_3$S$_2$ Observed: 471.1625

NMR(δ, CDCl$_3$): 2.58–2.85 (12H, m), 2.83(2H, 5, J=6 Hz), 3.67–3.70(2H, m), 3.94(2H, s), 6.51(1H, d, J=6 Hz), 6.87–6.91(2H, m), 7.04(1H, dd, J=9 Hz, 9 HZ), 7.15(1H, s), 7.18(1H, dd, J=5 Hz, 1 Hz), 7.31(1H, s), 7.69(1H, s)

EXAMPLE 21-34

Reactions between carboxylic acid compound and amine compound were conducted in the same manner as in Example 20 to obtain the following amide derivatives.

EXAMPLE 21

N-[2-[4-(4-chlorodiphenylmethylthio)ethyl-1-piperazinyl]ethyl]-5-acetoxy-3-hydroxy-2-naphthamide

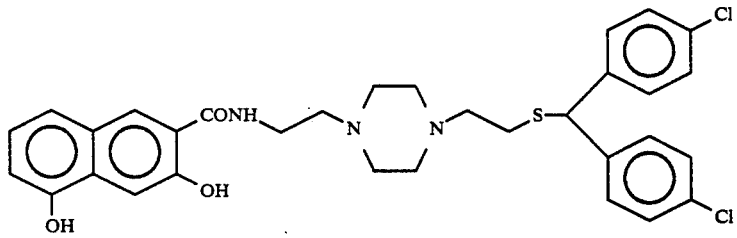

Yield: 65%

IR(cm$^{-1}$, CHCl$_3$): 1660

Mass spectromety Calculated: 609.1619 as C$_{32}$H$_{33}$O$_3$N$_3$SCl$_2$ Observed: 609.1644

NMR(δ, CDCl$_3$): 2.45–2.83(12H,m), 2.81(2H, t, J=6 Hz), 3.66–3.68(2H, m), 5.11(1H, s), 6.40(1H, d, J=6 Hz), 7.01(1H, dd, J=8 Hz, 8 Hz), 7.08–7.12(2H, m), 7.2314 7.31(9H, m), 7.58(1H, s)

EXAMPLE 22

N-[2-[4-(benzhydrylthio)ethyl-1-piperazinyl]ethyl]-3,5-dihydroxy-2-naphthamide

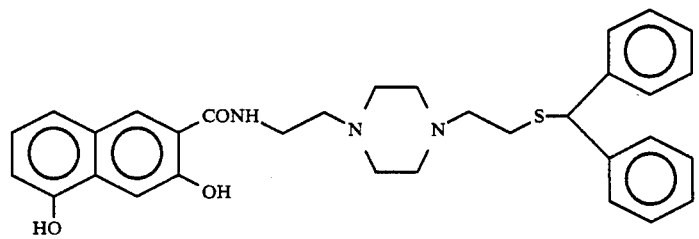

Yield: 74%
IR (cm⁻¹, CHCl₃): 1680
Mass spectrometry Calculated: 541.2398 as C₃₂H₃₅O₃N₃S Observed: 541.2397
NMR(δ, CDCl₃): 2.47–2.80(14H, m), 3.6514 3.67(2H, m), 5.18(1H, s), 6.40(1H, d, J=7 Hz), 7.00(1H, dd, J=8 Hz, 8 Hz), 7.10(1H, d, J=8 Hz), 7.17–7.30(12H, m), 7.38–7.41(4H, m), 7.57(1H, s)

EXAMPLE 23

N-[2-[4-(5-chloro-2-thienylmethylthio)ethyl-piperazinyl]ethyl]-3,5-dihydroxy-2-naphthamide

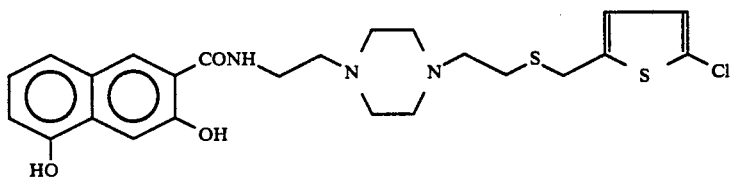

Yield: 75%
IR(cm⁻¹, CHCl₃): 1680
Mass spectrometry Calculated: 507.1229 as C₂₄H₂₈O₃N₃S₂Cl Observed: 507/1202
NMR(δ, CDCl₃): 2.57–2.83(14H, m), 2.82(2H, t, J=6 Hz), 3.70(2H, t, J=6 Hz), 3.82(2H, s), 6.46(1H, d, J=8 Hz), 6.67–6.69(2H, m), 7.03(1H, dd, J=9 Hz, 9 Hz), 7.11–7.15(2H, m), 7.61(1H, s)

EXAMPLE 24

N-[2-(4-benzhydryl-1-piperazinyl)ethyl]-3,5-dihydroxy-naphthamide

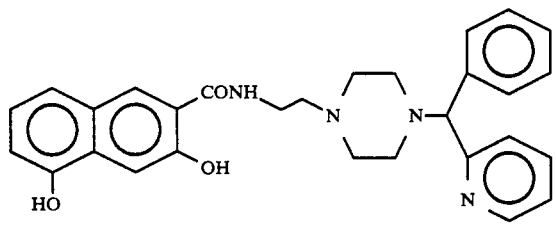

Yield: 71%
IR(cm⁻¹, CHCl₃): 1680
Mass spectrometry Calculated: 481.2365 as C₃₀H₃₁O₃N₃ Observed: 481.2358
NMR(δ, CDCl₃): 2.58–2.88(10H, m), 3.68(2H, br-s), 4.22(1H, s), 6.40(1H, d, J=7 Hz), 6.98(1H, dd, J=8 Hz, 8 Hz), 7.08(1H, d, J=8 Hz), 7.14–7.26(8H, m), 7.40(4H, d, J=7 Hz), 7.60(1H, s)

EXAMPLE 25

N-[2-[4-(2-pyridyl-phenylmethyl)piperazino]ethyl]-3,5-dihydroxy-2-naphthamide

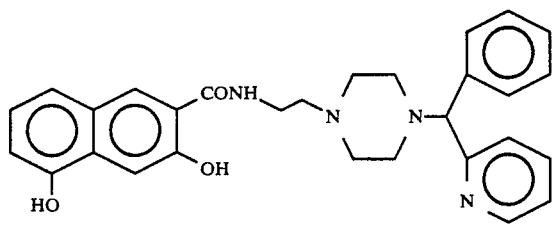

Yield: 72%
IR(cm⁻¹, CHCl₃): 1680
Mass spectromety Calculated: 482.2317 as C₂₉H₃₀O₃N₄ Observed: 482.2296
NMR(δ, CDCl₃): 2.50–2.70(4H, m), 2.72–2.86(6H, m), 3.66–3.71(2H, m), 4.47(1H, s), 6.66(1H, d, J=8 Hz), 6.99(1H, dd, J=8 Hz), 7.10–7.30(5H, m), 7.45–7.55(3H, m), 7.65(2H, ddd, J=8 Hz, 8 Hz, 2H), 7.72(1H, br-s), 7.82(1H, s), 8.52(1H, d, J=6 Hz)

EXAMPLE 26

N-[2-[4-(3-pyridyl-phenylmethyl)piperazino]ethyl]-3,5-dihydroxy-2-naphthamide

Yield: 71%
IR(cm⁻¹, CHCl₃): 1680
Mass spectrometry Calculated: 482.2317 as C₂₉H₃₀O₃N₄ Observed: 482.2307
NMR(δ, CDCl₃) 2.48–2.70(10H, m), 3.57(2H, t, J=6 Hz), 4.40(1H, s), 6.79 (1H, d, J=8 Hz), 7.11(1H, dd, J=8 Hz, 8 Hz), 7.22(1H, d, J=5 Hz), 7.28–7.42(5H, m), 7.43(2H, d, J=8 Hz), 7.55(1H, s), 7.93(1H, dd, J=8 Hz, 2 Hz), 8.32(1H, s), 8.37(1H, dd, J=5 Hz, 3 Hz), 8.60(1H, d, J-2 Hz)

EXAMPLE 27

N-[2-[4-(4-pyridyl-phenylmethyl)piperazino]ethyl]-3,5-dihydroxy-2-naphthamide

Yield: 62%
IR(cm⁻¹, CHCl₃): 1660
Mass spectrometry Calculated: 482.2318 as C₂₉H₃₀O₃N₄ Observed: 482.2319
NMR(δ, CDCl₃): 2.45–2.68(10H, m), 3.58(2H, t, J=6 Hz), 4.33(1H, s), 6.80(1H, d, J=6 Hz), 7.11(1H, dd, J=8 Hz, 8 Hz), 7.22(1H, d, J=8 Hz), 7.19–7.32(4H, m), 7.40(2H, d, J=7 Hz), 7.52(2H, d, J=6 Hz), 7.56(1H, s), 8.33(1H, s), 8.41(2H, d, J=6 Hz)

EXAMPLE 28

N-[2-[4-(2-pyridyl-phethylmethylthio)ethyl-1-piperazinyl]ethyl]-3,5-dihydroxy-2-naphthamide

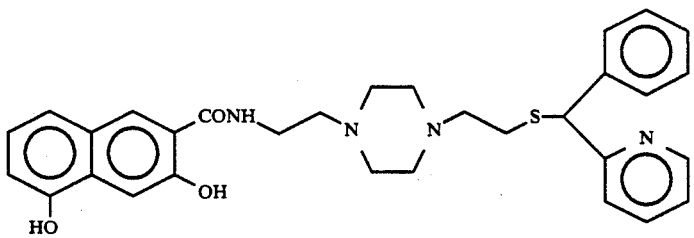

Yield: 54%
IR(cm$^{-1}$, CHCl$_3$): 1670
Mass spectrometry Calculated: 542.2351 as C$_{31}$H$_{34}$O$_3$N$_4$S Observed: 542.2380
NMR(δ, CDCl$_3$) 2.52–2.77(12H, m), 2.75(2H, t, J=5 Hz), 3.64(2H, t, J=5 Hz), 5.33(1H, s), 6.53(1H, d, J=6 Hz), 6.99–7.08(2H, m), 7.11–7.16(1H, m), 7.21–7.32(4H, m), 7.39(1H, s), 7.44–7.48(2H, m), 7.60–7.65(2H, m), 8.54(1H, d, J-3 Hz)

EXAMPLE 29

N-[2-[4-[(4-chlorophenyl)-phenylmethylthio]ethyl-1-piperazinyl]-3,5-dihydroxy-2-naphthamide

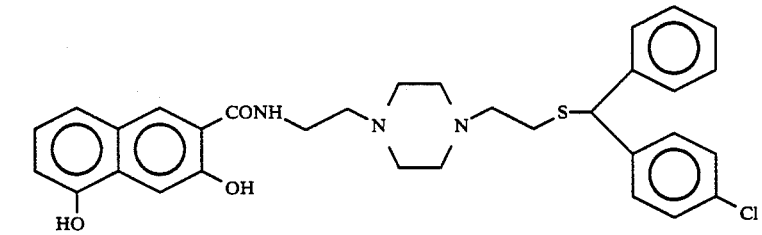

Yield: 70%
IR(cm$^{-1}$, CHCl$_3$): 1670
Mass spectromety Calculated: 575.2008 as C$_{32}$H$_{34}$O$_3$N$_3$ClS Observed: 575.1999

NMR(δ, CDCl$_3$) 2.48–2.80(12H, m), 2.78(2H, 5, J=5 Hz), 3.67(2H, t, J=5 Hz), 5.14(1H, s), 6.37(1H, d, J=7 Hz), 6.98–7.10(3H, m), 7.20–7.36(10H, m), 7.55(1H, s)

EXAMPLE 30

N-[2-[4-(2-thienyl-phenylmethylthio)ethyl-1-piperazinyl]ethyl]-3,5-dihydroxy-2-naphthamide

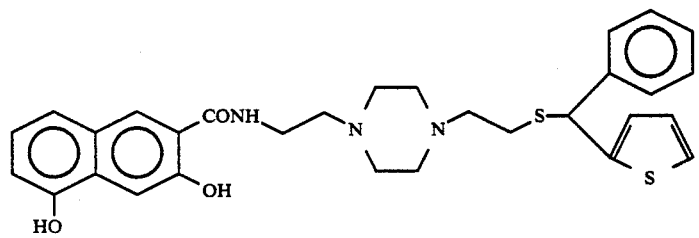

Yield: 71%
IR(cm$^{-1}$, CHCl$_3$): 1680
Mass spectromety Calculated: 547.1963 as C$_{30}$H$_{33}$O$_3$N$_3$S$_2$ Observed: 547.1963
NMR(δ, CDCl$_3$) 2.56–2.82(12H, m), 2.80(2H, t, J=6 Hz), 3.66(2H, t, J=6 Hz), 5.40(1H, s), 6.43(1H, d, J=6 Hz), 6.88–6.92(2H, m), 6.9914 7.14(3H, m), 7.19(1H, d, J=2 Hz), 7.20–7.33(4H, m), 7.43(2H, d, J=7 Hz), 7.59(1H, s)

EXAMPLE 31

N-[2-[4-(phenylmethylthio)ethyl-1-piperazinyl]ethyl-3,5-dihydroxy-2-naphthamide

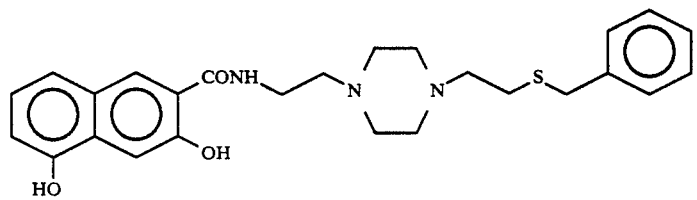

Yield: 70%
IR (cm$^{-1}$, CHCl$_3$)=1680

Mass spectrometry Calculated: 465.2086 as $C_{26}H_{31}O_3N_3S$ Observed: 465.2098

NMR(δ, CDCl$_3$): 2.53–2.84 (14H,m), 2.82 (2H,t,J=6 Hz), 3.71 (2H,s), 6.47 (1H,d,J=7 Hz), 7.02 (1H,dd,J=8 Hz,8 Hz), 7.13 (1H,d,J=8 Hz), 7.11–7.29 (7H,m), 7.65 (1H,s)

EXAMPLE 32

N-[2-[4-[2-(2-thienyl)ethylthio]ethyl-1-piperazinyl]-ethyl]-3,5-dihydroxy-2-naphthamide

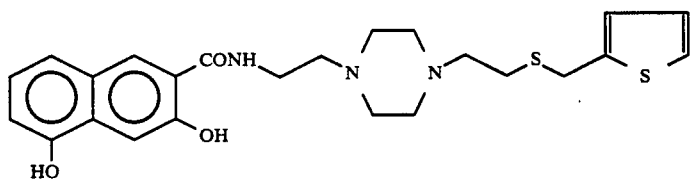

Yield: 58%
IR (cm$^{-1}$, CHCl$_3$)=1680
Mass spectrometry Calculated: 485.1807 as $C_{25}H_{31}O_3N_3S$ Observed: 485.1818

NMR(δ, CDCl$_3$): 2.58–2.85 (16H,m), 3.09 (2H,t,J=8 Hz), 3.68 (2H,t,J=6 Hz), 6.45 (1H,d,J=8 Hz), 6.82 (1H,d,J=3 Hz), 6.90–6.92 (1H,m), 7.02 (1H,dd,J=8 Hz,8 Hz), 7.11–7.15 (3H,m), 7.27 (1H,s), 7.61 (1H,s)

EXAMPLE 33

N-[2-[4-(furfurylthio)ethyl-1-piperazinyl]ethyl]-3,5-dihydroxy-naphthamide

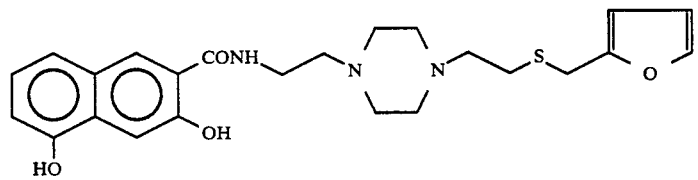

Yield: 53%
IR (cm$^{-1}$, CHCl$_3$)=1680
Mass spectrometry Calculated: 455.1878 as $C_{24}H_{29}O_4N_3S$ Observed: 455.1857

NMR(δ, CDCl$_3$): 2.55–2.83 (14H,m), 3.67–3.75 (2H,m), 3.73 (2H,s), 6.15 (1H,d,J=3 Hz), 6.27 (1H,dd,J=3 Hz), 6.46 (1H,d,J=8 Hz), 7.02 (1H,dd,J=8 Hz,8 Hz), 7.12 (1H,d,J=8 Hz), 7.16 (1H,br-s), 7.28 (1H,s), 7.33 (1H,s), 7.62 (1H,s)

EXAMPLE 34

N-[2-[4-(benzhydryloxy)piperidino]ethyl]-3,5-dihydroxy-2-naphthamide

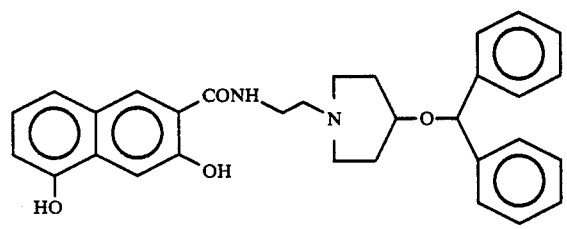

Yield: 73%
IR (cm$^{-1}$, KBr)=1660
Mass spectrometry Calculated: 496.2360 as $C_{31}H_{32}O_4N_2$ Observed: 496.2352

NMR(δ, CDCl$_3$): 1.86–1.90 (2H,m), 1.97–1.99 (2H,m), 2.57–2.62 (2H,m), 2.83 (2H,t,J=6 Hz), 2.94 (2H,t,J=6 Hz), 3.57–3.67 (3H,m), 5.48 (1H,s), 6.40 (1H,d,J=8 Hz), 6.97 (1H,dd,J=8 Hz,8 Hz), 7.05 (1H,d,J=8 Hz), 7.19–7.32 (1H,m), 7.58 (1H,s)

EXAMPLE 35

Synthesis of N-[2-[4-(benzhydryloxy)piperidino]ethyl]-3,7-dihydroxy-2-naphthamide

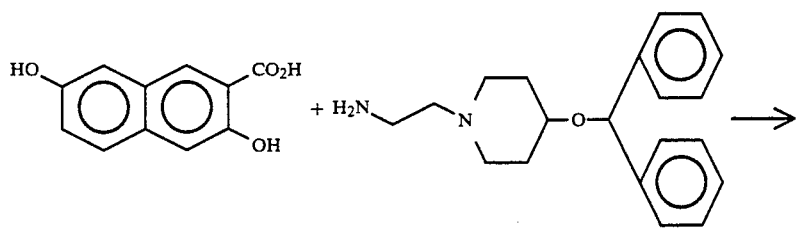

-continued

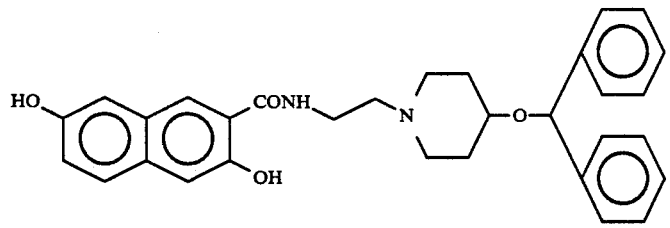

408 mg (2.0 mM) of 3,7-dihydroxy-2-naphthoic acid was dissolved in 20 ml of dichloromethane. Thereto were added 235 mg (2.0 mM) of N-hydroxysuccinimide and 422 mg (2.0 mM) of dicyclohexylcarbodiimide. The mixture was stirred at room temperature for 1 hour. Thereto was dropwise added a solution of 620 mg (2.0 mM) of 1-(2-aminoethyl)-4-(benzhydroloxy)piperidine in 20 ml of dichloromethane. The resulting mixture was stirred at room temperature for 2 hours to give rise to a reaction. After the completion of the test, extraction with dichloromethane was conducted. The extract was washed with a saturated aqueous sodium hydrogencarbonate solution and a saturated aqueous sodium chloride solution two times, and dried over anhydrous sodium sulfate solution. The solvent was removed by distillation. The residue was mixed with 20 ml of acetonitrile. The mixture was filtered and the filtrate was subjected to distillation to remove the solvent. The residue was purified by silica gel chromatography to obtain 725 mg of the title compound at a yield of 73%.

IR (cm$^{-1}$, CHCl$_3$) = 1670

Mass spectrometry Calculated: 496.2360 as C$_{31}$H$_{32}$O$_4$N$_2$ Observed: 496.2350

NMR(δ, CDCl$_3$) 1.88–1.92 (2H,m), 1.98–2.04 (2H,m), 2.45–2.60 (2H,m), 2.79 (2H,t,J=5 Hz), 2.95 (2H,t,J=4 Hz), 3.56–3.61 (1H,m), 3.65–3.69 (2H,m), 5.50 (1H,s), 6.81 (1H,dd,J=9 Hz,5 Hz), 7.03 (2H,d,J=4 Hz), 7.25–7.33 (11H,m), 7.65 (1H,s), 7.75 (1H,br-s)

EXAMPLE 36–39

Reactions between carboxylic acid compound and amine compound were conducted in the same manner as in Example 4 to obtain the following amide derivatives.

EXAMPLE 36

N-[2-[4-(benzhydryloxy)piperidino]ethyl]-3-hydroxy-2-naphthamide

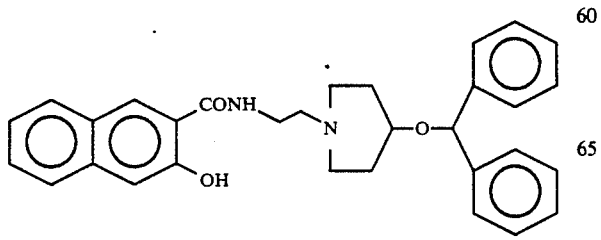

Yield: 53%

IR (cm$^{-1}$, KBr) = 1660

Mass spectrometry Calculated: 480.2411 as C$_{31}$H$_{32}$O$_3$N$_2$ Observed: 480.2382

NMR(δ, CDCl$_3$): 1.78–1.89 (2H,m), 1.98–2.04 (2H,m), 2.33–2.38 (2H,m), 2.68 (2H,t,J=5 Hz), 2.88 (2H,t,J=5 Hz), 3.52–3.60 (3H,m), 5.54 (1H,s), 7.22–7.38 (13H,m), 7.47 (1H,dd,J=7 Hz,7 Hz), 7.67 (1H,d,J=8 Hz), 7.78 (1H,d,J=8 Hz), 7.98 (1H,s)

EXAMPLE 37

N-[2-[4-(benzhydryloxy)piperidino]ethyl]-5-methoxy-3-hydroxy-2-naphthamide

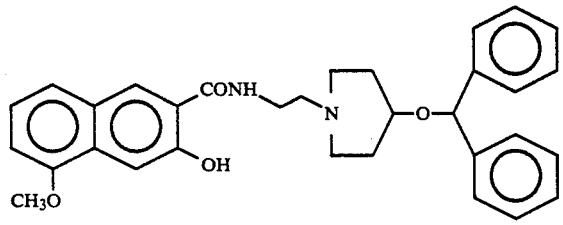

Yield: 78%

IR (cm$^{-1}$, KBr) = 1660

Mass spectrometry Calculated: 510.2527 as C$_{32}$H$_{34}$O$_4$N$_2$ Observed: 510.2495 NMR(δ, CDCl$_3$): 1.78–1.90 (2H,m), 1.98–2.03 (2H,m), 2.25–2.42 (2H,m), 2.40–2.68 (2H,m), 2.87 (2H,t,J=5 Hz), 3.52–3.59 (3H,m), 3.97 (3H,s), 5.53 (1H,s), 6.79 (2H,d,J=8 Hz), 7.18 (12H,m), 7.59 (1H,br-s), 7.70 (1H,s), 7.83 (1H,s)

EXAMPLE 38

N-[2-[4-(2-thienylmethylthio)ethyl-1-piperazinyl]-ethyl]-3-hydroxy-5-methoxy-2-naphthamide

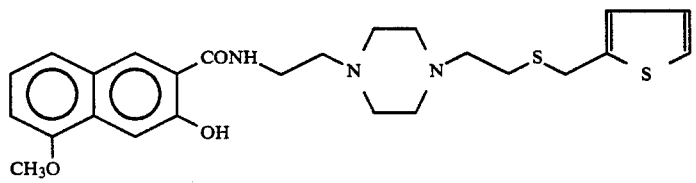

Yield: 61%

IR (cm$^{-1}$, KBr) = 1660

Mass spectrometry Calculated: 485.1805 as C$_{25}$H$_{31}$O$_3$N$_2$S Observed: 485.1789

NMR(δ, CDCl$_3$) 2.55–2.68 (14H,m), 3.55–3.58 (2H,m), 3.96 (2H,s), 3.98 (3H,s), 6.80 (1H,d,J=8 Hz), 6.90–6.94 (2H,m), 7.19–7.25 (2H,m), 7.35 (2H,d,J=9 Hz), 7.70 (1H,s), 7.89 (1H,s)

EXAMPLE 39

N-[2-[4-(benzhydryloxy)piperidino]ethyl]-3,5-dimethoxyl]-2-naphthamide

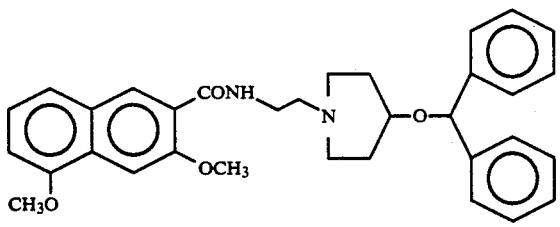

Yield: 66%
IR (cm$^{-1}$, KBr)=1660
Mass spectrometry Calculated: 524.2675 as C$_{33}$H$_{36}$O$_4$N$_2$ Observed: 524.2697
NMR(δ, CDCl$_3$): 1.63 (1H,br-s), 1.75–1.81 (2H,m), 1.97–2.08 (2H,m), 2.62 (2H,br-s), 2.87–2.88 (2H,m), 3.46–3.63 (2H,m), 4.01 (3H,s), 4.08 (3H,s), 5.54 (1H,s), 6.86 (1H,d,J=8 Hz), 7.23–7.35 (11H,m), 7.48 (1H,d,J=8 Hz), 7.61 (1H,s), 8.57 (1H,br-s), 8.70 (1H,s)

EXAMPLE 40

Synthesis of
N-[2-[4-(benzhydryloxy)piperidino]ethyl]-3-hydroxy-5-(2-pyridylmethoxyl)-2-naphthamide

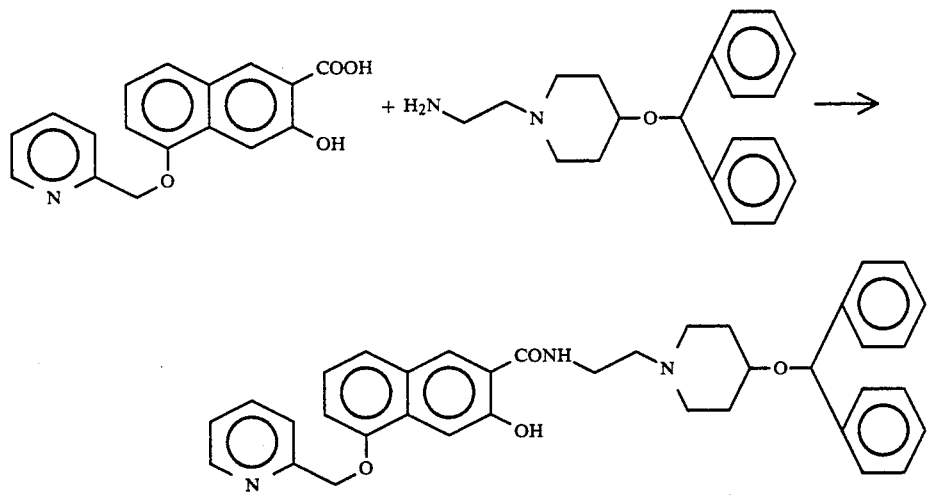

591 mg (2.0 mM) of 5-(2-pyridylmethoxy)3-hydroxy-2-naphthoic acid was dissolved in 20 ml of dichloromethane. Thereto were added 235 mg (2.0 mM) of N-hydroxysuccinimide and 422 mg (2.0 mM) of dicyclocarbodiimide. The resulting mixture was stirred at room temperature for 1 hour. Thereto was dropwise added a solution of 620 mg (2.0 mM) of 1-(2-aminoethyl)-4-(benzhydryloxy)-piperidine in 20 ml of dichloromethane. Stirring was conducted at room temperature for 2 hours to give rise to a reaction. After the completion of the reaction, extraction with dichloromethane was conducted. The extract was washed with a saturated aqueous sodium hydrogencarbonate solution and a saturated aqueous sodium chloride solution two times, and dried over anhydrous sodium sulfate. The solvent was removed by distillation. The residue was mixed with 20 ml of acetonitrile. The mixture was filtered, and the filtrate was subjected to distillation to remove the solvent. The residue was purified by silica gel chromatography to obtain 632 mg of the title compound at a yield of 67%.

IR (cm$^{-1}$, KBr)=1660
Mass spectrometry Calculated: 587.2783 as C$_{37}$H$_{37}$O$_4$N$_3$ Observed: 587.2812
NMR(δ, CDCl$_3$): 1.77–1.82 (2H,m), 1.96–2.03 (2H,m), 2.21–2.35 (2H,m), 2.21–2.35 (2H,m), 2.65 (2H,t,J=6 Hz), 2.82–2.89 (2H,m), 3.52–3.58 (3H,m), 5.36 (2H,s), 5.54 (1H,s), 6.87 (1H,d,J=8 Hz), 7.18–7.41 (13H,m), 7.50 (1H,d,J=8 Hz), 7.75 (1H,ddd,J=8 Hz,8 Hz,2 Hz), 7.84 (1H,s), 7.93 (1H,s), 8.61 (1H,d,J=6 Hz)

EXAMPLES 41–43

Reactions between carboxylic acid compound and amine compound were conducted in the same manner as in Example 40 to obtain the following amide derivatives.

EXAMPLE 41

N-[2-[4-(benzhydryloxy)piperidino]ethyl]-3hydroxy-5-[2-(2-pyridyl)ethoxy]-2-naphthamide

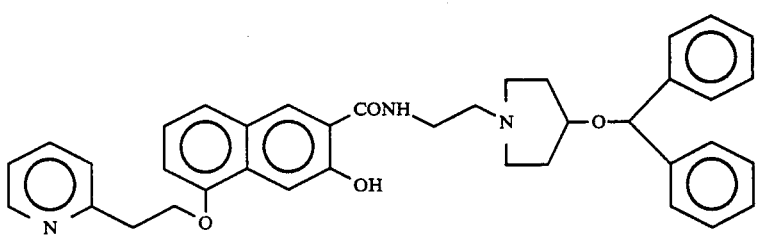

Yield: 62%
IR (cm$^{-1}$, KBr)=1660
Mass spectrometry Calculated: 601.2940 as C$_{38}$H$_{39}$O$_4$N$_3$ Observed: 601.2955

EXAMPLE 43

N-[2-[4-(benzhydryloxy)piperidino]ethyl]-3-hydroxy-5-(4-pyridylmethoxyl)-2-naphthamide

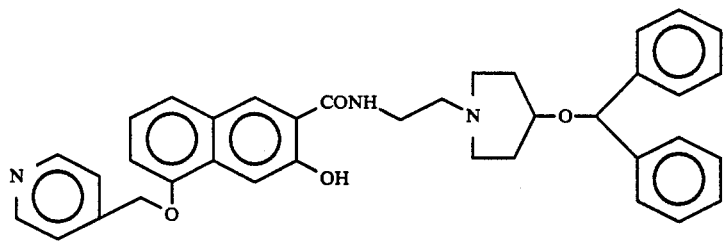

Yield: 52%
IR (cm$^{-1}$, KBr)=1660
Mass spectrometry Calculated: 587.2783 as C$_{37}$H$_{37}$O$_4$N$_3$ Observed: 587.2799
NMR(δ, CDCl): 1.77–1.81 (2H,m), 1.95–2.01 (2H,m), 2.20–2.35 (2H,m), 2.65 (2H,t,J=6 Hz), 2.87 (2H,t,J=6 Hz), 3.51–3.58 (3H,m), 5.24 (2H,s), 5.54 (1H,s), 6.81 (1H,t,J=8 Hz), 7.18–7.37 (12H,m), 7.41 (1H,s), 7.45 (2H,t,J=6 Hz), 7.81 (1H,s), 7.94 (1H,s), 8.65 (2H,t,J=6 Hz)

NMR(δ, CDCl$_3$): 1.74–1.83 (2H,m), 1.90–2.00 (2H,m), 2.17–2.30 (2H,m), 2.62 (2H,t,J=6 Hz), 2.80–2.86 (2H,m), 3.39 (2H,t,J=6 Hz), 3.46–3.55 (3H,m), 4.51 (2H,t,J=6 Hz), 5.54 (1H,s), 6.83 (1H,d,J=8 Hz), 7.13–7.40 (14H,m), 7.63 (1H,s), 7.66 (1H,dd,J=6 Hz,2 Hz), 7.85 (1H,s), 8.56 (1H,d,J=5 Hz)

EXAMPLE 42

N-[2-[4-(benzhydryloxy)piperidino]ethyl]-3-hydroxy-5-(3-pyridylmethoxyl)-2-naphthamide

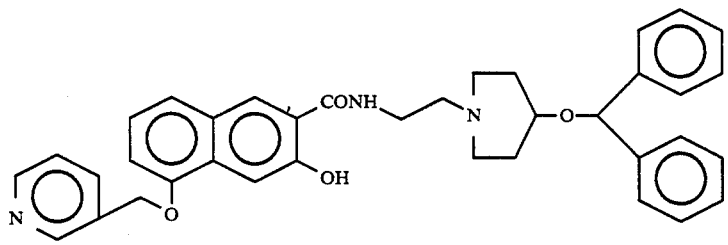

Yield: 65%
IR (cm$^{-1}$, KBr)=1660
Mass spectrometry Calculated: 587.2783 as C$_{37}$H$_{37}$O$_4$N$_3$ Observed: 587.2760
NMR(δ, CDCl$_3$): 1.70–1.85 (2H,m), 1.92–2.03 (2H,m), 2.18–2.30 (2H,m), 2.63 (2H,t,J=6 Hz), 2.81–2.92 (2H,m), 3.37–3.57 (3H,m), 5.23 (2H,s), 5.54 (1H,s), 6.88 (1H,d,J=7 Hz), 7.19–7.42 (14H,m), 7.55 (1H,br-s), 7.71 (1H,s), 7.89 (1H,d,J=7 Hz), 7.94 (1H,s), 8.62 (1H,dd,J=6 Hz,2 Hz), 8.74 (1H,d,J=2 Hz)

EXAMPLE 44

Synthesis of N-[5-(2-thienylmethylthio)pentyl]-3,5-dihydroxy-2-naphthamide

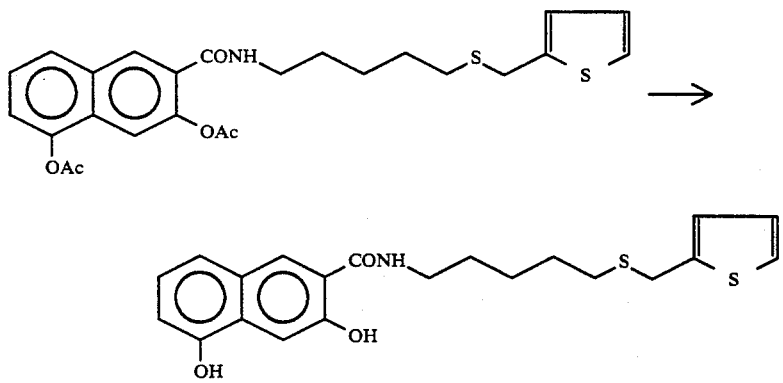

1.2 g (2.5 mM) of the compound of Example 1 was dissolved in 40 ml of methanol. Thereto was dropwise added, with ice cooling, a solution of 346 mg (2.5 mM) of potassium carbonate in 5 ml of water. The resulting mixture was stirred at room temperature for 1 hour to give rise to a reaction. After the completion of the reaction, the solvent was removed by distillation. The residue was subjected to extraction with chloroform. The extract was washed with water and a saturated aqueous sodium chloride solution, and dried over anhydrous sodium sulfate. The solvent was removed by distillation. The residue was purified by silica gel chromatography to obtain 853 mg of the title compound at a yield of 85%.

IR (cm$^{-1}$, KBr)=1660

Mass spectrometry Calculated: 401.1118 as $C_{21}H_{23}O_3NS_2$ Observed: 401.1110

NMR(δ, CDCl$_3$): 1.48-1.51 (2H,m), 1.58-1.68 (4H,m), 2.52 (2H,t,J=7 Hz), 3.48 (2H,dt,J=6 Hz,6 Hz), 3.92 (2H,s), 6.65 (1H,br-s), 6.83 (1H,d,J=7 Hz), 6.90-6.91 (2H,s), 7.13 (1H,dd,J=7 Hz,7 Hz), 7.19 (1H,d,J=5 Hz,2 Hz), 7.33 (1H,d,J=7 Hz), 7.62 (1H,s), 7.91 (1H,s)

EXAMPLE 45

N-[3-(2-thienylmethylthio)propyl]-3,5-dihydroxy-2-naphthamide

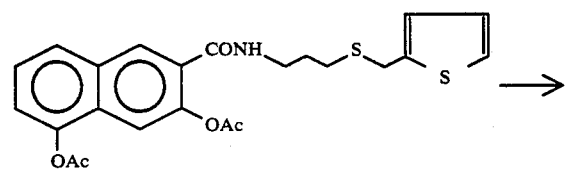 →

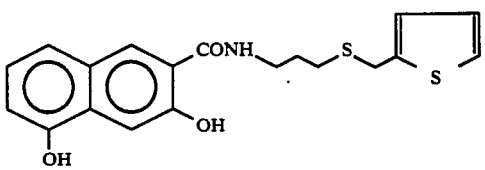

The compound of Example 2 was reacted in the same manner as in Example 44 to obtain the title compound at a yield of 68%.

IR (cm$^{-1}$, KBr)=1660

Mass spectrometry Calculated: 373.0842 as $C_{19}H_{19}O_3NS_2$ Observed: 373.0824

NMR(δ, CDCl$_3$): 1.95 (2H,tt,J=8 Hz,8 Hz), 2.65 (2H,t,J=8 Hz), 3.60 (2H,dt,J=8 Hz,8 Hz), 3.97 (2H,s), 6.83-6.93 (3H,m), 7.15 (1H,d,J=8 Hz), 7.17 (1H,dd,J=5 Hz,2 Hz), 7.62 (1H,s), 7.87 (1H,s)

EXAMPLES 46-71

The compounds shown in Table 4 were produced in the same manners as in Example 1-45. The properties of these compounds are shown in Table 5.

TABLE 4

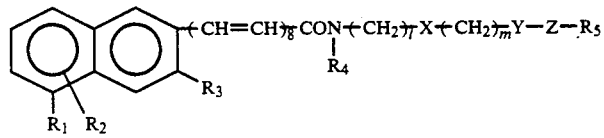

| Example No. | $R_1$ | $R_2$ | $R_3$ | q | $R_4$ | l | X | m | Y | Z | $R_5$ |
|---|---|---|---|---|---|---|---|---|---|---|---|
| 46 | OH | H | OH | 0 | H | 2 | —N⟨piperazine⟩N— | 2 | S | CH$_2$ | 4-Cl-C$_6$H$_4$ |
| 47 | OH | H | OH | 0 | H | 2 | —N⟨piperazine⟩N— | 2 | S | CH$_2$ | 4-F-C$_6$H$_4$ |
| 48 | OH | H | OH | 0 | H | 2 | —N⟨piperazine⟩N— | 2 | S | CH$_2$ | 4-CH$_3$-C$_6$H$_4$ |
| 49 | OH | H | OH | 0 | H | 2 | —N⟨piperazine⟩N— | 2 | S | CH$_2$ | 2,3-Cl$_2$-C$_6$H$_3$ |
| 50 | OH | H | OH | 0 | H | 2 | —N⟨piperazine⟩N— | 2 | S | CH$_2$ | 4-NO$_2$-C$_6$H$_4$ |

TABLE 4-continued

Structure: Naphthalene with R1, R2 on one ring and R3 on the other, with substituent (CH=CH)q-CON(R4)-(CH2)l-X-(CH2)m-Y-Z-R5

| Example No. | R1 | R2 | R3 | q | R4 | l | X | m | Y | Z | R5 |
|---|---|---|---|---|---|---|---|---|---|---|---|
| 51 | OH | H | OH | O | H | 2 | piperazine | 2 | S | $CH_2$ | 3,5-bis(CF$_3$)-phenyl |
| 52 | OH | H | OH | O | H | 2 | piperazine | 2 | S | $CH_2$ | 4-OCH$_3$-phenyl |
| 53 | OH | H | OH | O | H | 2 | piperazine | 2 | S | $CH_2$ | 4-Br-phenyl |
| 54 | OH | H | OH | O | H | 2 | piperazine | 2 | S | $CH_2$ | 4-CN-phenyl |
| 55 | OH | H | OH | O | H | 2 | piperazine | 2 | S | $CH_2$ | 4-CH(CH$_3$)$_2$-phenyl |
| 56 | OH | H | OH | O | H | 2 | piperazine | 2 | S | $CH_2$ | 4-C(CH$_3$)$_3$-phenyl |
| 57 | OH | H | OH | O | H | 2 | piperazine | 2 | S | $CH_2$ | 4-SCH$_3$-phenyl |
| 58 | OH | H | OH | O | H | 2 | piperazine | 2 | S | $CH_2$ | benzo[1,3]dioxole |
| 59 | OH | H | OH | O | H | 2 | piperazine | 2 | S | $CH_2$ | 4-F-phenyl |
| 60 | OH | H | OH | O | H | 2 | piperazine | 2 | S | $CH_2$ | 4-COOC$_2$H$_5$-phenyl |
| 61 | OH | H | OH | O | H | 2 | piperazine | 2 | S | $CH_2$ | 4-COCH$_3$-phenyl |

TABLE 4-continued

Structure:

Naphthalene-(CH=CH)$_q$-CON(R$_4$)-(CH$_2$)$_l$-X-(CH$_2$)$_m$-Y-Z-R$_5$, with R$_1$, R$_2$ on one ring and R$_3$ on the other.

| Example No. | R$_1$ | R$_2$ | R$_3$ | q | R$_4$ | l | X | m | Y | Z | R$_5$ |
|---|---|---|---|---|---|---|---|---|---|---|---|
| 62 | OH | H | OH | O | H | 2 | piperazine (-N N-) | 2 | S | CH$_2$ | biphenyl |
| 63 | OH | H | OH | O | H | 2 | piperazine (-N N-) | 2 | S | Single bond | 4-F-phenyl |
| 64 | OH | H | OH | O | H | 2 | piperazine (-N N-) | 2 | S | Single bond | phenyl |
| 65 | OH | H | OH | O | H | 2 | piperazine (-N N-) | 2 | S | Single bond | 4-Cl-phenyl |
| 66 | OH | H | OH | O | H | 2 | piperazine (-N N-) | 2 | S | Single bond | 4-OCH$_3$-phenyl |
| 67 | OH | H | OH | O | H | 2 | piperazine (-N N-) | 2 | S | Single bond | 3,4-diCl-phenyl |
| 68 | OH | H | OH | O | H | 2 | piperazine (-N N-) | 2 | S | Single bond | naphthyl |
| 69 | OH | H | OH | O | H | 2 | piperazine (-N N-) | 2 | CH$_2$ | Single bond | 3,4-diCl-phenyl |
| 70 | OH | H | OH | O | H | 1 | —CH$_2$— | 0 | S | Single bond | naphthyl |
| 71 | OH | H | OH | O | H | 2 | homopiperazine (-N N-) | 2 | S | CH$_2$ | thienyl |

TABLE 5

| Example No. | IR (cm$^{-1}$, CHCl$_3$) | NMR (δ, CDCl$_3$) | Yield |
|---|---|---|---|
| 46 | 1660 (KBr) | 2.54–2.70 (12H, m), 2.78 (2H, t, J=6Hz), 3.63–3.68 (4H, m) 6.52 (1H, d, J=8Hz), 7.05 (1H, dd, J=8Hz, 8Hz), 7.12 (1H, br-S) 7.18 (1H, d, J=8Hz), 7.21–7.26 (4H, m), 7.31 (1H, S), 7.65 (1H, S) | 70 |

TABLE 5-continued

| Example No. | IR (cm$^{-1}$, CHCl$_3$) | NMR (δ, CDCl$_3$) | Yield |
|---|---|---|---|
| 47 | 1680 (KBr) | 2.54–2.64 (8H, m), 2.77–2.85 (7H, m), 3.69 (4H, S), 6.52 (1H, d, J=8Hz), 6.95–7.06 (2H, m), 7.16 (1H, d, J=9Hz), 7.23–7.28 (1H, m), 7.32 (1H, S), 7.71 (1H, S) | 68 |
| 48 | 1670 (KBr) | 2.30 (3H, S), 2.55–2.84 (15H, m), 3.68 (4H, S), 6.54 (1H, d, J=7Hz), 7.01–7.11 (3H, m), 7.34 (1H, S), 7.73 (1H, S) | 65 |
| 49 | 1660 (KBr) | 2.50–2.90 (14H, m), 3.65 (2H, S), 3.65–3.75 (2H, m), 6.51 (1H, d, J=7Hz), 7.03 (1H, dd, J=7Hz), 7.10–7.20 (2H, m), 7.31 (1H, S), 7.35 (1H, d, J=7Hz), 7.69 (1H, S) | 59 |
| 50 | 1660 1510 (KBr) | 2.51–2.80 (14H, m), 3.66 (2H, dt, J=5Hz, 5Hz), 3.79 (2H, S) 6.49 (1H, d, J=8Hz), 7.04 (1H, dd, J=8Hz, 8Hz), 7.15 (1H, d, J=9Hz), 7.31 (1H, S), 7.47 (2H, d, J=9Hz), 7.61 (1H, S), 8.15 (2H, d, J=9Hz) | 57 |
| 51 | 1660 (KBr) | 2.53–2.83 (12H, m), 2.82 (2H, t, J=5Hz), 3.68 (2H, dt, J=5Hz, 5Hz), 3.82 (2H, S), 6.46 (1H, d, J=6Hz), 7.02 (1H, dd, J=7Hz, 7Hz), 7.12 (1H, d, J=6Hz), 7.26 (1H, S), 7.63 (1H, S), 7.78 (3H, S) | 72 |
| 52 | 1670 (KBr) | 2.54–2.82 (14H, m), 2.81 (2H, t, J=4Hz), 3.68 (3H, S), 3.78 (2H, S), 6.49 (1H, d, J=8Hz), 6.83 (2H, d, J=9Hz), 7.48 (1H, dd, J=8Hz, 8Hz), 7.16 (1H, d, J=8Hz), 7.20 (1H, brs) 7.22 (2H, d, J=9Hz), 7.30 (1H, S), 7.65 (1H, S) | 73 |
| 53 | 1660 (KBr) | 2.51–2.84 (14H, m), 3.66–3.69 (4H, m), 6.54 (1H, d, J=7Hz), 7.05 (1H, dd, J=7Hz, 7Hz), 7.17 (3H, d, J=8Hz), 7.32 (1H, br-S), 7.34 (1H, S), 7.41 (2H, d, J=9Hz), 7.72 (1H, S) | 75 |
| 54 |  | 2.56–2.68 (14H, m), 3.60 (2H, t, J=6Hz), 3.83 (2H, S), 6.80 (1H, d, J=8Hz), 7.13 (1H, dd, J=8Hz, 8Hz), 7.32 (1H, d, J=9Hz), 7.53 (2H, d, J=9Hz), 7.68 (2H, d, J=9Hz), 8.33 (1H, S) | 65 |
| 55 | 1670 (KBr) | 1.21 (6H, d, J=7Hz), 2.56–2.82 (17H, m), 3.69 (2H, S), 6.57 (1H, d, J=8Hz), 7.01 (1H, dd, J=8Hz, 8Hz), 7.15 (2H, d, J=8Hz), 7.19 (2H, d, J=5Hz), 7.22 (2H, d, J=5Hz), 7.32 (1H, br-S), 7.36 (1H, S), 7.74 (1H, S) | 61 |
| 56 | 1660 (KBr) | 1.29 (3H, S), 2.57–2.83 (16H, m), 3.70 (2H, S), 6.58 (1H, d, J=7Hz), 7.06 (1H, dd, J=8Hz, 8Hz), 7.20 (1H, d, J=5Hz), 7.22 (1H, br-S), 7.25 (2H, d, J=8Hz), 7.31 (2H, d, J=8Hz), 7.37 (1H, S), 7.45 (1H, S) | 63 |
| 57 | 1660 (KBr) | 2.46 (3H, S), 2.51–2.82 (16H, m), 3.68 (2H, S), 6.55 (1H, d, J=7Hz), 7.08 (1H, dd, J=8Hz, 8Hz), 7.18–7.27 (4H, m), 7.20 (2H, d, J=5Hz), 7.35 (1H, S), 7.72 (1H, S) | 70 |
| 58 | 1660 (KBr) | 2.56–2.81 (15H, m), 3.64 (2H, S), 3.66 (2H, t, J=6Hz), 5.93 (2H, S), 6.53 (1H, d, J=8Hz), 6.71 (2H, S), 6.83 (1H, S), 7.05 (1H, dd, J=9Hz, 9Hz), 7.18 (1H, d, J=9Hz), 7.25 (1H, br-S), 7.33 (1H, S), 7.70 (1H, S) | 59 |
| 59 | 1680 (KBr) | 1.20 (3H, t, J=8Hz), 2.50–2.85 (14H, m), 3.60–3.7 (2H, m,), 3.70 (2H, S), 6.49 (1H, d, J=7Hz), 7.00–7.35 (9H, m), 7.61 (1H, S) | 72 |
| 60 | 1720 1660 (KBr) | 1.39 (3H, t, J=7Hz), 2.49–2.83 (14H, m), 3.67(2H, t, J=7Hz), 3.74 (2H, S), 4.36 (2H, t, J=7Hz), 6.45 (1H, d, J=7Hz), 7.02 (1H, dd, J=7Hz, 7Hz), 7.12 (1H, d, J=8Hz), 7.28 (1H, S), 7.36 (2H, d, J=8Hz), 7.61 (1H, S), 7.97 (2H, d, J=8Hz) | 80 |
| 61 | 1690 1660 (KBr) | 2.48–2.60 (10H, m), 2.57 (3H, S), 2.80–2.89 (6H, m), 3.73 (2H, S), 6.58 (1H, d, J=8Hz), 7.01 (1H, dd, J=8Hz), 7.11 (1H, d, J=8Hz), 7.37 (2H, d, J=8Hz), 7.62 (1H, br-S), 7.44 (1H, S), 7.88 (2H, d, J=8Hz) | 66 |
| 62 | 1660 (KBr) | 2.50–2.75 (14H, m), 3.60–3.72 (2H, m), 3.76 (2H, S), 6.58 (2H, d, J=7Hz), 7.06 (1H, dd, J=7Hz, 7Hz), 7.18–7.47 (6H,m), 7.47–7.60 (4H, m), 67.74 (1H, S) | 69 |
| 63 | 1680 (KBr) | 2.61–2.73 (14H, m), 3.05 (2H, t, J=7Hz), 3.61 (2H, t, J=7Hz), 6.79 (1H, d, J=8Hz), 7.03–7.14 (3H, m), 7.30 (1H, d, J=9Hz), 7.41–7.46 (2H, m), 7.55 (1H, S), 8.32 (1H, S) | 78 |
| 64 | 1670 (KBr) | 2.64–2.83 (13H, m), 3.04 (2H, t, J=7Hz), 3.67 (2H, dt, J=5Hz, 5Hz), 6.49 (1H, d, J=6Hz), 7.02 (1H, dd, J=7Hz, 7Hz), 7.12–7.19 (2H, m), 7.24–7.34 (5H, m), 7.66 (1H, S) | 74 |
| 65 | 1660 (KBr) | 2.63–2.82 (12H, m), 3,00 (2H, t, J=7Hz), 3.68 (2H, dt, J=5Hz, 5Hz), 6.43 (1H, d, J=7Hz), 6.99–7.14 (3H, m), 7.25 (4H, d, J=8Hz), 7.59 (1H, S) | 71 |
| 66 | 1660 (KBr) | 2.61–2.82 (12H, m), 2.92–2.96 (2H, m), 3.67–3.68 (2H, dt, J=8Hz), 3.79 (3H, S), 6.49 (1H, d, J=7Hz), 6.83 (2H, d, J=9Hz), 7.04 (1H, dd, J=8Hz, 8Hz), 7.15 (1H, d, J=8Hz), 7.19 (1H, br-S), 7.29 (1H, S), 7.34 (2H, d, J=9Hz), 7.65 (1H, S) | 73 |
| 67 | 1680 (KBr) | 7.65–2.86 (12H, m), 3.03 (2H, t, J=7Hz), 3.69 (2H, br-S), 6.56 (1H, d, J=7Hz), 7.05 (1H, dd, J=7Hz, 7Hz), 7.13 (1H, dd, J=9Hz, 2Hz), 7.20 (1H, d, J=9Hz), 7.31 (1H, S), 7.34 (1H, d, J=3Hz), 7.41 (1H, d, J=2Hz) | 70 |
| 68 | 1660 (KBr) | 2.70–2.82 (12H, m), 3.15 (2H, t, J=7Hz), 3.67 (2H, dt, J=5Hz, 5Hz), 6.56 (1H, d, J=7Hz), 7.03 (1H, dd, J=8Hz, 8Hz), 7.17 (1H, d, J=8Hz), 7.34 (1H, br-S), 7.35 (1H, S), 7.40–7.47 (3H, m), 7.71–7.79 (5H, m) | 62 |
| 69 | 1660 (KBr) | 1.70–1.85 (2H, m), 2.37 (2H, t, J=8Hz), 2.50–3.85 (12H, m), 3.67 (2H, br-S), 6.48 (1H, d, J=7Hz), 7.00 (1H, dd, J=7Hz, 2Hz), 7.05 (1H, d, J=7Hz), 7.15 (2H, d, J=7Hz), 7.32 (2H, d, J=7Hz), 7.64 (1H, S) | 61 |

TABLE 5-continued

| Example No. | IR (cm⁻¹, CHCl₃) | NMR (δ, CDCl₃) | Yield |
|---|---|---|---|
| 70 | 1680 (KBr) | 3.34 (2H, t, J=7Hz), 3.81 (2H, dt, J=7Hz, 7Hz), 6.80 (1H, dd, J=7Hz, 2Hz), 6.84 (1H, br-S), 7.03–7.10 (2H, m), 7.40–7.60 (4H, m), 7.70–7.80 (2H, m), 7.90 (1H, dd, J=2Hz) | 75 |
| 71 | 1680 (KBr) | 1.85–2.00 (2H, m), 2.50–3.00 (12H, m), 3.61 (2H, br-S), 3.88 (2H, S), 6.58 (1H, d, J=6.8Hz), 6.85 (2H, d, J=3Hz), 7.00 (1H, dd, J=7Hz, 7Hz), 7.05 (1H, d, J=7Hz), 7.17 (1H, m), 7.36 (1H, S), 7.72 (1H, S) | |

EXAMPLE 72

N-[2-(4-benzhydrylpiperazino)ethyl]-3-hydroxy-5-(3-pyridylmethoxy)-2-naphthamide

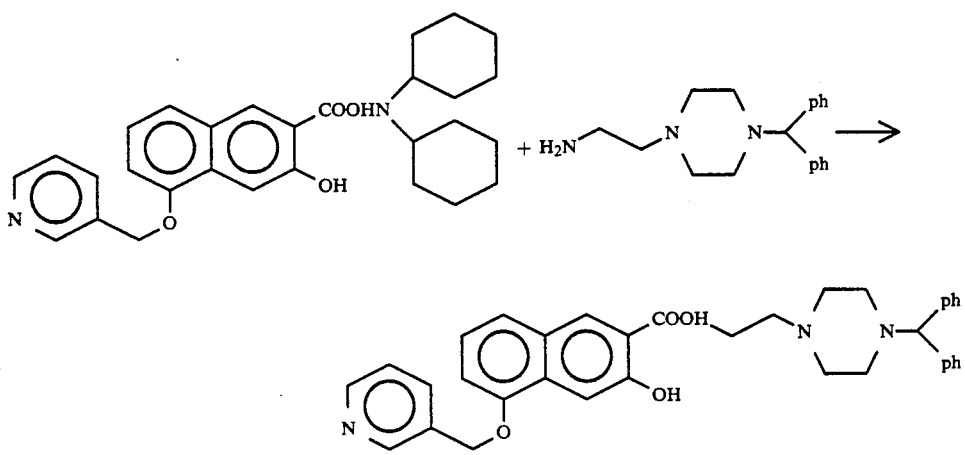

19.1 g (40.0 mM) of dicyclohexylamine salt of 3-hydroxy 5-(3-pyridylmethoxy)-2-naphtoic acid was dissolved in 11.2 ml (80.0 mM) of triethylamine and 500 ml of anhydrous methylene chloride. Thereto was dropwise added, at −20° C., a solution of 9.6 ml (80.0 mM) of pivaloyl chloride in 10 ml of anhydrous methylene chloride. The resulting mixture was stirred for 2 hours. Thereto was dropwise added a solution of 17.4 g (56.0 mM) of 2-(4-benzhydrylpiperazino)ethaneamine in 20 ml of anhydrous methylene chloride. The mixture was stirred for 2 hours. The reaction mixture was washed with water and then with a saturated aqueous sodium chloride solution, and dried over anhydrous sodium sulfate. The solvent was removed by distillation under reduced pressure. The residue was dissolved in 600 ml of methanol. Thereto was added 160 ml of an aqueous solution containing 16.56 g (120.0 mM) of potassium carbonate. Stirring was conducted at room temperature for 1 hour. The solvent was removed by distillation under reduced pressure. The residue was dissolved in 1000 ml of ethyl acetate. The solution was washed with water, a saturated aqueous ammonium chloride solution and a saturated aqueous sodium chloride solution in this order, and dried over anhydrous sodium sulfate. The solvent was removed by distillation under reduced pressure. The residue was purified by silica gel chromatography to obtain 18.3 g of the title compound at a yield of 78%. The properties of the compound are shown in Table 7.

The compounds shown in Table 6 were produced in the same manner as in Example 72. The properties of these compounds are shown in Table 7.

TABLE 6

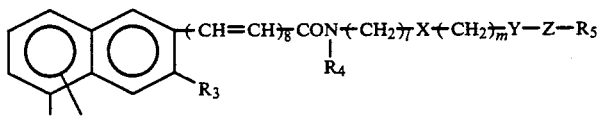

| Example No. | R₁ | R₂ | R₃ | q | R₄ | l | X | m | Y | Z | R₅ |
|---|---|---|---|---|---|---|---|---|---|---|---|
| 72 | OCH₂-(3-pyridyl) | H | OH | 0 | H | 2 | -N(piperazine)N- | 0 | Single bond | CH | (diphenyl) |

TABLE 6-continued

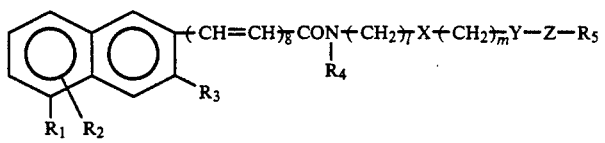

| Example No. | R₁ | R₂ | R₃ | q | R₄ | l | X | m | Y | Z | R₅ |
|---|---|---|---|---|---|---|---|---|---|---|---|
| 73 | 3-pyridyl-CH₂O- | H | OH | 0 | | | piperazine | 0 | Single bond | CH-phenyl | phenyl |
| 74 | 3-pyridyl-CH₂O- | H | OH | 0 | H | 4 | piperazine | 0 | Single bond | CH-phenyl | phenyl |
| 75 | 3-pyridyl-CH₂O- | H | OH | 0 | H | 2 | 4-piperidyl | 0 | O | CH-phenyl | 4-Cl-phenyl |
| 76 | 3-pyridyl-CH₂O- | H | OH | 0 | | | 4-piperidyl | 0 | O | CH-phenyl | phenyl |
| 77 | 3-pyridyl-CH₂O- | H | OH | 0 | H | 4 | 4-piperidyl | 0 | O | CH-phenyl | phenyl |
| 78 | 3-pyridyl-CH₂O- | H | OH | 0 | H | 2 | homopiperazine | 0 | Single bond | CH-phenyl | phenyl |
| 79 | 3-pyridyl-CH₂O- | H | OH | 0 | H | 2 | piperazine | 0 | Single bond | CH-phenyl | 4-Cl-phenyl |
| 80 | 3-pyridyl-CH₂O- | H | OH | 0 | H | 2 | N(CH₃) | 2 | O | CH-phenyl | phenyl |

TABLE 7

| Example No. | IR (cm⁻¹, CHCl₃) | NMR (δ, CDCl₃) | Yield |
|---|---|---|---|
| 72 | 1650 (KBr) | 2.54–2.76 (10H, m), 3.60–3.62 (2H, m), 4.29 (1H, S), 5.24 (2H, S), 6.89 (1H, d, J=5Hz), 7.18–7.44 (13H, m), 7.73 (1H, S), 7.90 (1H, d, J=8Hz), 8.10 (1H, S), 8.64 (1H, dd, J=5Hz, 2Hz), 8.74 (1H, d, J=2Hz) | 68 |
| 73 | 1640 (KBr) | 2.46–2.50 (4H, m), 3.78–3.82 (4H, m), 4.28 (1H, S), 5.21 (2H, S), 6.86 (1H, d, J=8Hz), 7.18–7.43 (13H, m), 7.68 (1H, S), 7.74 (1H, S), 7.87 (1H, d, J=9Hz), 8.61 (1H, dd, J= | 67 |

TABLE 7-continued

| Example No. | IR (cm$^{-1}$, CHCl$_3$) | NMR (δ, CDCl$_3$) | Yield |
|---|---|---|---|
| | | 6Hz, 3Hz), 8.73 (1H, d, J=2Hz) m.p. 110.5–119.8° C. | |
| 74 | 1660 (KBr) | 1.69–1.77 (4H, m), 2.44–2.60 (10H, m), 3.49–3.52 (2H, m), 4.10 (1H, S), 5.25 (2H, S), 6.89 (1H, d, J=6Hz), 7.13–7.40 (13H, m), 7.74 (1H, S), 7.91 (1H, d, J-8Hz), 8.06 (1H, S), 8.62 (1H, d, J=5Hz), 8.75 (1H, d, J=2Hz) | 65 |
| 75 | 1660 (KBr) | 1.80–1.83 (2H, m), 1.99–2.05 (2H, m), 2.35–2.50 (2H, m), 2.70–2.82 (2H, m), 2.87–2.93 (2H, m), 3.50–3.65 (3H, m), 5.24 (2H, m), 5.49 (1H, S), 6.88 (1H, d, J=8Hz), 7.18–7.44 (12H, m), 7.73 (1H, S), 7.90 (1H, d, J=8Hz), 8.02 (1H, S), 8.62 (1H, dd, J=5Hz, 2Hz), 8.74 (1H, d, J=2Hz) | 53 |
| 76 | 1660 (KBr) | 1.84–1.91 (4H, m), 3.63–3.66 (2H, m), 3.75–3.78 (H, m), 3.94–4.03 (2H, m), 5.24 (2H, S), 5.54 (1H, S), 6.87 (1H, d, J=8Hz), 7.20–7.42 (13H, m), 7.71 (1H, S), 7.76 (1H, S), 7.94 (1H, d, J=8Hz), 8.61 (1H, d, J=5Hz), 8.76 (1H, S) | 87 |
| 77 | 1660 (KBr) | 1.73–1.84 (6H, m), 1.93–1.99 (2H, m), 2.25–2.40 (2H, m), 2.44–2.53 (2H, m), 2.81–2.90 (2H, m), 3.49–3.54 (3H, m), 5.23 (2H, S), 5.48 (1H, S), 6.86 (1H, d, J=7Hz), 7.12 (1H, dd, J=8Hz, 8Hz), 7.24–7.43 (12H, m), 7.73 (1H, S), 7.90 (1H, d, J=8Hz), 8.08 (1H, S), 8.62 (1H, dd, J=5Hz, 2Hz), 8.74 (1H, d, J=2Hz) | 68 |
| 78 | 1660 (KBr) | 1.82–1.89 (2H, m), 2.69–2.93 (10H, m), 3.55 (2H, t, J=6Hz), 4.61 (1H, S), 5.24 (2H, S), 6.88 (1H, d, J=5Hz), 7.14–7.28 (8H, m), 7.35–7.41 (5H, m), 7.44 (1H, S), 7.91 (1H, d, J=5Hz), 8.00 (1H, S), 8.62 (1H, dd, J=5Hz, 2Hz), 8.74 (1H, d, J=2Hz) | 75 |
| 79 | 1660 (KBr) | 2.45–2.62 (8H, m), 2.67 (2H, t, J=6Hz), 3.55–3.60 (2H, m), 4.24 (1H, S), 5.23 (2H, S), 6.88 (1H, d, J=8Hz), 7.20–7.31 (5H, m), 7.34–7.39 (6H, m), 7.42 (1H, br-S), 7.72 (1H, s), 7.89 (1H, d, J=8Hz), 7.90 (1H, S), 8.62 (1H, dd, J=8Hz, 2Hz), 8.74 (1H, d, J=2Hz) | 75 |
| 80 | 1660 (KBr) | 2.40 (3H, S), 2.76–2.83 (4H, m), 3.57–3.66 (4H, m), 5.23 (2H, S), 5.37 (1H, S), 6.86 (1H, dd, J=4Hz, 4Hz), 7.12–7.39 (13H, m), 7.58 (1H, S), 7.71 (1H, S), 7.83 (1H, S), 7.91 (1H, d, J=8Hz), 8.61 (1H, dd, J=4Hz, 2Hz), 8.74 (1H, d, J=2Hz) | 78 |

| Preparation Example A Tablets Composition of one tablet | |
|---|---|
| (1) Compound of Example 42 | 50 mg |
| (2) Corn starch | 30 mg |
| (3) Lactose | 113.4 mg |
| (4) Hydroxypropyl cellulose | 6 mg |
| (5) Water | 0.03 ml |
| (6) Magnesium stearate | 0.6 mg |

The components (1), (2), (3) and (4) were mixed. The component (5) was added thereto, and kneading was conducted. The kneaded product was vacuum-dried at 40° C. for 16 hours.

The resulting product was ground and passed through a 16-mesh sieve to obtain granules. The component (6) was added to the granules, and the mixture was made into tablets (200 mg per tablet) using a rotary type tablet-manufacturing machine manufactured by Kikusui Seisakusho.

| Preparation Example B Enteric tablets | |
|---|---|
| (1) Compound of Example 42 | 50 mg |
| (2) Corn starch | 30 mg |
| (3) Lactose | 113.4 mg |
| (4) Hydroxycellulose | 6 mg |
| (5) Water | 0.03 ml |
| (6) Magnesium stearate | 0.6 mg |
| (7) Cellulose acetate phthalate | 10 mg |
| (8) Acetone | 0.2 ml |

Tablets were produced in the same manner as in Preparation Example A using the components (1), (2), (3), (4), (5) and (6).

The tablets were coated with an acetone solution of the component (7) using a bar coater manufactured by FREUND to produce enteric tablets (210 mg per tablet).

| Preparation Example C Capsules Composition of one capsule | |
|---|---|
| (1) Compound of Example 42 | 30 mg |
| (2) Corn starch | 40 mg |
| (3) Lactose | 74 mg |
| (4) Hydroxypropyl cellulose | 6 mg |
| (5) Water | 0.02 ml |

The components (1), (2), (3) and (4) were mixed. The component (5) was added thereto, and kneading was conducted. The kneaded product was vacuum-dried at 40° C. for 16 hours. The product was ground and passed through a 16-mesh sieve to obtain granules. The granules were filled into gelatin No. 3 capsules using a capsule filler manufactured by SANACI of Italia, to produce capsules.

| Preparation Example D injection | |
|---|---|
| (1) Compound of Example 42 | 5 mg |
| (2) Sodium salicylate | 50 mg |
| (3) Sodium chloride | 180 mg |
| (4) Sodium metabisulfite | 20 mg |
| (5) Methylparaben | 36 mg |
| (6) Propylparaben | 4 mg |
| (7) distilled water for injection | 2 ml |

The components (2), (3), (4), (5) and (6) were dissolved in about half of the component (7) at 80° C. with stirring. The resoluting solution was cooled to 40° C., and the component (1) was dissolved thereinto. Thereto was added the rest of the component (7) to adjust to a final volume. The solution was subjected to sterile filtration using an appropriate filter paper to obtain an injection.

We claim:

1. A naphthoic acid derivative represented by formula (I-1):

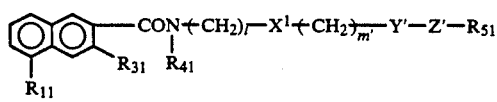
(I-1)

wherein $R_{11}$ is a hydroxyl group, a lower alkanoyloxy group or a pyridyl-substituted lower alkoxy group;

$R_{31}$ is a hydroxyl group or a lower alkanoyloxy group; $R_{41}$ is a hydrogen atom;

$R_{51}$ is a phenyl group, a halophenyl group or a thienyl group;

$X^1$ is

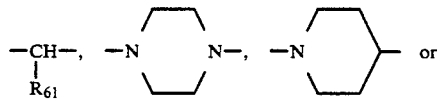

where $R_{61}$ is a hydrogen atom, or $R_{61}$ together with $R_{41}$, may form an alkylene of 1–2 carbon atoms;

$Y^1$ is —S—, —O— or a single bond;

$Z^1$ is —CH$_2$— or

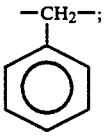

$l$ is an integer of 0–4; and $m'$ is an integer of 0–4; or a pharmaceutically acceptable salt thereof.

2. The compound of claim 1 wherein $R_{11}$ is a pyridylmethoxy group;
$R_{31}$ is a hydroxyl group;
$R_{41}$ is a hydrogen atom;
$R_{51}$ is a Phenyl group;
$X^1$ is

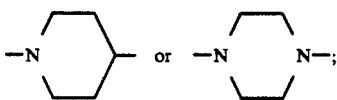

$Y^1$ is —O— or a single bond;
$Z^1$ is

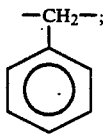

$l$ is 2–4; and
$m'$ is 0.

3. An antiallergic composition comprising an antiallergically effective amount of a naphthoic acid derivative of the formula (I) in claim 1 or a pharmaceutically acceptable salt thereof and a pharmaceutically acceptable carrier or diluent.

4. A method for treating an allergosis patient, which comprises administering to the patient an effective amount of a naphthoic acid derivative represented by the formula described in claim 1 or a pharmaceutically acceptable salt thereof.

* * * * *